United States Patent
Bacque et al.

(10) Patent No.: US 7,560,565 B2
(45) Date of Patent: Jul. 14, 2009

(54) METHOD FOR PREPARING DERIVATIVES OF 3-HYDROXYPICOLINIC ACID

(75) Inventors: Eric Bacque, Morsang sur Orge (FR); Jean-Pierre Vors, Lyons (FR); Francisco Nieto-Roman, Palencia (ES); Alain Villier, St. Didier au Mont d'Or (FR); Jean-Claude Barriere, Bures sur Yvette (FR); William Henri Barriere, legal representative, Bures-sur Yvette (FR); Nathalie Hélène Barriere, legal representative, Bures-sur Yvette (FR)

(73) Assignees: Bayer Cropscience SA (FR); Aventis Pharma SA (FR)

( * ) Notice: Subject to any disclaimer, the term of this patent is extended or adjusted under 35 U.S.C. 154(b) by 591 days.

(21) Appl. No.: 10/169,855

(22) PCT Filed: Jan. 8, 2001

(86) PCT No.: PCT/FR01/00044

§ 371 (c)(1), (2), (4) Date: Jul. 8, 2005

(87) PCT Pub. No.: WO01/49667

PCT Pub. Date: Jul. 12, 2001

(65) Prior Publication Data

US 2006/0040995 A1    Feb. 23, 2006

(30) Foreign Application Priority Data

Jan. 6, 2000 (FR) .................................. 00 00140

(51) Int. Cl.
*C07D 213/78* (2006.01)

(52) U.S. Cl. ........................................................ 546/298
(58) Field of Classification Search .................... None
See application file for complete search history.

(56) References Cited

FOREIGN PATENT DOCUMENTS

| EP | 1013169 | 6/2000 |
| WO | 9525723 | 9/1995 |
| WO | 0026191 | 5/2000 |

OTHER PUBLICATIONS

U.S. Appl. No. 10/181,842, filed Jul. 8, 2002, Nieto-Roman et al.
T.. Sakamoto, et al. "Site-selectivity in the cyanation of 3-substituted pyridine 1-oxides with trimethylsilanecarbonitrile" Chemical and Pharmaceutical Bulletin., vol. 33, No. 2, 1985, pp. 565-571, XP 002166800, Pharmaceutical Society of Japan. Tokyo, JP, ISSN: 0009-2363.
Database WPI, Section Ch. Week 199944, Derwent Publications Ltd., London, GB; AN 1999-522674, XP002150334, & JP 11 228542 A (Meiji Seika Kaisha Ltd), Aug. 24, 1999.

*Primary Examiner*—Zinna N Davis
(74) *Attorney, Agent, or Firm*—Ostrolenk Faber LLP

(57) ABSTRACT

The invention concerns a method for preparing compounds of general formula (I) wherein: n, $Q_1$, $Q_2$, $X_1$, $X_2$, Y and Z are as defined in the description.

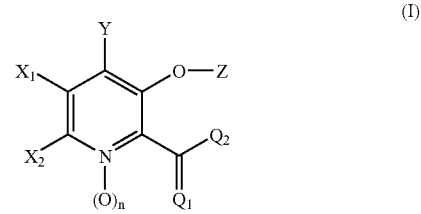

(I)

23 Claims, No Drawings

METHOD FOR PREPARING DERIVATIVES OF 3-HYDROXYPICOLINIC ACID

The Applicants claim priority to International Application Number PCT/FR01/00044, filed on Jan. 8, 2001, and French Application Number 00/00140, filed on Jan. 6, 2000.

The present invention relates to a new process for preparing derivatives of 3-hydroxypicolinic acid, and more particularly of picolinic acid derivatives substituted in position 3 with an oxygen atom and optionally substituted in position 4.

Such 3-hydroxypicolinic acid derivatives are known in the literature and in particular in patent application WO-A-99/11127 and in the publication by Kuzo Shibata et al. (*The Journal of Antibiotics,* 51 (12), (1998), 1113-1116), for their fungicidal properties against phytopathogenic fungi of plants.

However, the preparation processes presented do not, for example, allow access to 3-hydroxypicolinic acid derivatives substituted in position 4. Specifically, the compounds described in these publications are obtained from fermentation musks of natural compounds.

Other 3-hydroxypicolinamide derivatives are also known from patent application publications JP-11 228 542 and EP-A-0 690 061. There again the preparation-processes presented do not give access to all the derivatives in the present description.

Thus, the present invention concerns a new process for preparing 3-hydroxypicolinic acid derivatives of general formula (I):

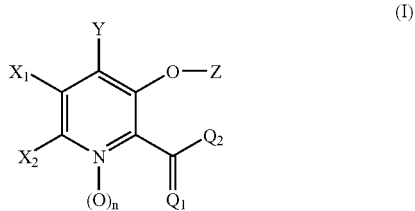

in which:
n represents 0 or 1,
$Q_1$ is chosen from an oxygen or sulfur atom, a group $NR_1$ and a group $N—NR_4R_5$,
$Q_2$ is chosen from a group $OR_2$ or $SR_3$ and a group $—NR_4R_5$, or
$Q_1$ and $Q_2$ may together form a ring of 5 to 7 atoms containing 2 to 3 oxygen and/or nitrogen atoms, optionally substituted with one or more radicals, which may be identical or different, chosen from halogens and alkyl and haloalkyl radicals,
Z is chosen from a hydrogen atom, a cyano radical and an alkyl, allyl, aryl, arylalkyl, propargyl, cycloalkyl, halocycloalkyl, alkenyl, alkynyl, cyanoalkyl, haloalkyl, alkoxyalkyl, haloalkoxyalkyl, alkylthioalkyl, haloalkylthioalkyl, N-alkylaminoalkyl, N,N-dialkylaminoalkyl, acylaminoalkyl, alkoxycarbonylaminoalkyl, aminocarbonylaminoalkyl, alkoxycarbonyl, N-alkylaminocarbonyl, N,N-dialkylaminocarbonyl, acyl, thioacyl, alkoxythiocarbonyl, N-alkylaminothiocarbonyl, N,N-dialkylaminothiocarbonyl, alkylsulfinyl, haloalkylsulfinyl, alkylsulfonyl, haloalkylsulfonyl, alkoxysulfonyl, aminosulfonyl, N-alkylaminosulfonyl, N,N-dialkylaminosulfonyl, arylsulfinyl, arylsulfonyl, aryloxysulfonyl, N-arylaminosulfonyl, N,N-diarylaminosulfonyl or N,N-arylalkylaminosulfonyl radical;

Y is chosen from a hydrogen atom, a halogen atom, a hydroxyl, mercapto, nitro, thiocyanato, azido, cyano or pentafluorosulfonyl radical, an alkyl, haloalkyl, alkoxy, haloalkoxy, alkylthio, haloalkylthio, alkoxyalkyl, haloalkoxyalkyl, alkylthioalkyl, haloalkylthioalkyl, cyanoalkyl, cyanoalkoxy, cyanoalkylthio, alkylsulfinyl, haloalkylsulfinyl, alkylsulfonyl, haloalkylsulfonyl or alkoxysulfonyl radical, a cycloalkyl, halocycloalkyl, alkenyl, alkynyl, alkenyloxy, alkynyloxy, alkenylthio or alkynylthio group, an amino, N-alkylamino, N,N-dialkylamino, —NH-$COR_{10}$, —NHCS$R_{10}$, N-alkylaminocarbonylamino, N,N-dialkylaminocarbonylamino, aminoalkyl, N-alkylaminoalkyl, N,N-dialkylaminoalkyl, acylaminoalkyl, thioacylamino, alkoxythiocarbonylamino, N-alkylaminothiocarbonylamino, N,N-dialkylaminothiocarbonylamino, N,N-arylalkylaminocarbonylamino, N-alkylsulfinylamino, N-alkylsulfonylamino, N-alkyl(alkylsulfonyl)amino, N-arylsulfinylamino, N-arylsulfonylamino, N-alkoxysulfonylamino, N-alkoxysulfinylamino, N-haloalkoxysulfinylamino, N-haloalkoxysulfonylamino, N-arylamino, N,N-diarylamino, arylcarbonylamino, alkoxycarbonylamino, N-arylaminocarbonylamino, N,N-diarylaminocarbonylamino, arylthiocarbonylamino, aryloxythiocarbonylamino, N-arylaminothiocarbonylamino, N,N-diarylaminothiocarbonylamino or N,N-arylalkylaminothiocarbonylamino group, an acyl, carboxyl, carbamoyl, N-alkylcarbamoyl, N,N-dialkylcarbamoyl, lower alkoxycarbonyl, N-arylcarbamoyl, N,N-diarylcarbamoyl, aryloxycarbonyl or N,N-arylalkylcarbamoyl radical, and an imino group of formula:

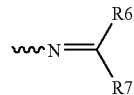

$X_1$ and $X_2$ are identical or different and chosen, independently of each other, from a hydrogen atom, a halogen atom, a hydroxyl, mercapto, nitro, thiocyanato, azido, cyano or pentafluorosulfonyl radical, and an alkyl, haloalkyl, alkoxy, haloalkoxy, alkylthio, haloalkylthio, alkoxyalkyl, haloalkoxyalkyl, alkylthioalkyl, haloalkylthioalkyl, cyanoalkyl, cyanoalkoxy, cyanoalkylthio, alkylsulfinyl, haloalkylsulfinyl, alkylsulfonyl, haloalkylsulfonyl or alkoxysulfonyl radical, or $X_1$ and $X_2$ may also be joined together, thus forming a saturated, partially unsaturated or totally unsaturated 4- to 8-membered ring optionally comprising one or more hetero atoms chosen from sulfur, oxygen, nitrogen and phosphorus, $R_2$ and $R_3$ are identical or different and chosen, independently of other, from an alkyl radical comprising from 1 to 12 carbon atoms, a haloalkyl, cycloalkyl, halocycloalkyl, alkoxy, haloalkoxy, alkylthio, haloalkylthio, alkoxyalkyl, haloalkoxyalkyl, alkylthioalkyl, haloalkylthioalkyl, cyanoalkyl or acyl radical, a nitro, cyano, carboxyl, carbamoyl or 3-oxetanyloxycarbonyl radical, and an N-alkylcarbamoyl, N,N-dialkylcarbamoyl, alkoxycarbonyl, alkylthiocarbonyl, haloalkoxycarbonyl, alkoxythiothiocarbonyl, haloalkokylthiothiocarbonyl, alkokythiothiocarbonyl, alkenyl, alkynyl, N-alkylamino, N,N-dialkylamino, N-alkylaminoalkyl or N,N-dialkylaminoalkyl radical, or a radical chosen from aryl, arylalkyl, heterocyclyl and heterocyclylalkyl, optionally substituted with one or more radicals $R_9$ and/or aryl and/or arylalkyl, which may be identical or different, and/or a group -T-$R_8$, or $R_1$, $R_4$, $R_5$, $R_6$ and $R_7$ are identical or different and chosen, independently of each other, from a hydrogen atom, an optionally substituted alkyl radical comprising from 1 to 12 carbon atoms in a linear or branched chain, a haloalkyl, cycloalkyl, halocycloalkyl, alkoxy, aryloxy, arylalkoxy, haloalkoxy, alkylthio, haloalkylthio, alkoxyalkyl, haloalkoxyalkyl, alkylthioalkyl, haloalkylthioalkyl, cyanoalkyl or acyl radical, a nitro, cyano, carboxyl, carbamoyl or 3-oxetanyloxycarbonyl radical, and an N-alkylcarbamoyl, N,N-dialkylcarbamoyl, alkoxycarbonyl, alkylthiocarbonyl, haloalkoxycarbonyl, alkoxythiocarbonyl, haloalkoxythiocarbonyl, alkylthiothiocarbonyl, alkenyl, alkynyl, N-alkylamino, N,N-dialkylamino, N-alkylaminoalkyl or N,N-dialkylaminoalkyl radical, or a radical chosen from aryl, arylalkyl, heterocyclyl and heterocyclylalkyl, optionally substituted with one or more radicals $R_9$ and/or aryl and/or arylalkyl, which may be identical or different, and/or a group -T-$R_8$, or $R_4$ and $R_5$, on the one hand, or $R_6$ and $R_7$, on the other hand, may be joined together, thus forming a saturated, partially unsaturated or totally unsaturated 4- to 8-membered ring optionally comprising one or more hetero atoms chosen from sulfur, oxygen, nitrogen and phosphorus, T represents a direct bond or a divalent radical chosen from a radical —$(CH_2)_m$—, m taking a value between 1 and 12, limits included, the said radical optionally being interrupted or ending with one or two hetero atoms chosen from nitrogen, oxygen and/or sulfur, and an oxyalkylene, alkoxyalkylene, carbonyl (—CO—), oxycarbonyl (—O—CO—), carbonyloxy (—CO—O—), sulfinyl (—SO—), sulfonyl (—$SO_2$—), oxysulfonyl (—O—$SO_2$—), sulfonyloxy (—$SO_2$O—), oxysulfinyl (—O—SO—), sulfinyloxy (—SO—O—), thio (—S—), oxy (—O—), vinyl (—C═C—), ethynyl (—C≡C—), —$NR_9$—, —$NR_9$—, —$ONR_9$—, —N═N—, —$NR_9$—$NR_{10}$—, —$NR_9$—S—, —$NR_9$—SO—, —$NR_9$—$SO_2$—, —S—$NR_9$—, —SO—$NR_9$—, —$SO_2$—$NR_9$—, —CO—$NR_9$—O— or —O—$NR_9$—CO— radical, $R_8$ is chosen from a hydrogen atom and an aryl or heterocyclyl radical, $R_9$ and $R_{10}$, which may be identical or different, are chosen, independently of each other, from a hydrogen atom, a halogen atom, a hydroxyl, mercapto, nitro, thiocyanato, azido, cyano or pentafluorosulfonyl radical, and an alkyl, haloalkyl, alkoxy, haloalkoxy, alkylthio, haloalkylthio, alkoxyalkyl, haloalkoxyalkyl, alkylthioalkyl, haloalkylthioalkyl, arylalkyl, cyanoalkyl, cyanoalkoxy, cyanoalkylthio, alkylsulfinyl, haloalkylsulfinyl, alkylsulfonyl, haloalkylsulfonyl or alkoxysulfonyl radical, as well as the optional N-oxides, geometrical and/or optical isomers, enantiomers and/or diastereoisomers, tautomeric forms, salts and metal and metalloid complexes of the compounds of formula (I) as have just been defined.

The tautomeric forms of the compounds of formula (I) such as those defined above are also included in the invention. By tautomeric forms there are to be understood all of the isomeric forms described in the work. "The Tautomerism of Heterocycles, Advances in Heterocyclic Chemistry, Supplement 1, by J Elguero, C. Martin, A. R. Katritsky and P Linda, published by Academic Press, New York, 1976, pages 1-4.

The following generic terms are used with the following meanings:

halogen atom signifies the fluorine, chlorine, bromine or iodine atom the alkyl radicals as well as groups including these alkyl radicals, (alkoxy, alkylcarbonyl or acyl, etc.) include, unless indicated to the contrary, from 1 to 6 carbons atoms in a linear or branched chain and are optionally substituted, the halogenated alkyl, alkoxy and halocycloalkyl radicals may comprise one or more identical or different halogen atoms, the cycloalkyl radicals comprise from 3 to 6 carbon atoms and are optionally substituted, the alkenyl and alkynyl radicals, as well as groups including such radicals, comprise, unless indicated to the contrary, from 2 to 6 carbon atoms in a straight or branched chain and are optionally substituted, the acyl radical signifies alkylcarbonyl or cycloalkylcarbonyl, the alkyl part containing from 1 to 6 carbon atoms and the cycloalkyl part containing 3 to 6 carbon atoms, unless indicated to the contrary and are optionally substituted, the alkylene radical designates the divalent —$(CH_2)_m$— radical where m represents an integer equal to 1, 2, 3, 4, 5 or 6, the term "aryl" in "aryl" and "arylalkyl" signifies phenyl or naphthyl, optionally substituted, the term "heterocyclyl" in "heterocyclyl" and "heterocyclylalkyl" signifies a ring of 4 to 10 members, saturated, partially unsaturated or unsaturated, optionally substituted, comprising one or more heteroatoms, identical or different, chosen from nitrogen, oxygen, sulfur, silicon and phosphorus, when the amino radical is disubstituted, the two substituents are identical or different or may together with the nitrogen atom which carries them form a saturated, partially unsaturated or unsaturated nitrogen-containing heterocycle, containing 5 or 6 atoms in total, when the carbamoyl radical is disubstituted, the two substituents are identical or different or may together with the nitrogen atom which carries them form a saturated, partially unsaturated or unsaturated nitrogen-containing heterocycle of 5 to 6 carbon atoms in total, unless indicated to the contrary, the expression "optionally substituted" qualifying an organic group applies to different radicals constituting the group and indicates that the different radicals are optionally substituted by one or more radicals R9 and/or aryl and/or arylalkyl, identical or different.

According to one variant of the present invention, the invention relates to a process for preparing 3-hydroxypicolinic acid derivatives of general formula (I) as defined above and for which:

$X_1$ and $X_2$ each represent a hydrogen atom,
the other substituents being as defined above,
as well as the optional N-oxides, geometrical and/or optical isomers, enantiomers and/or diastereoisomers, tautomeric forms, salts and metal and metalloid complexes of compounds of formula (I) as they have just been defined.

According to another variant of the present invention, this invention relates to a process for preparing 3-hydroxypicolinic acid derivatives of general formula (I) as defined above and for which:

$Q_1$ is chosen from an oxygen atom and a sulfur atom,
the other substituents being as previously defined, as well as the optional N-oxides, geometrical and/or optical isomers, enantiomers and/or diastereoisomers, tautomeric forms, salts and metal and metalloid complexes of compounds of formula (I) as they have just been defined.

According to a third variant of the present invention, this invention relates to 3-hydroxypicolinic acid derivatives of general formula (I) as defined above and for which:

Z is chosen from an alkyl radical and a hydrogen atom or a cleavable radical capable of donating hydrogen, for example an alkoxyalkyl, haloalkoxyalkyl, alkylthioalkyl, haloalkylthioalkyl, N-alkylaminoalkyl, N,N-dialkylaminoalkyl, acylaminoalkyl, acyl, thioacyl, cyanoalkyl, alkoxythiocarbonyl, N-alkylaminothiocarbonyl, N,N-dialkylaminothiocarbonyl or alkylsulfinyl radical, the other substituents being as defined above, as well as the optional N-oxides, geometrical and/or optical isomers, enantiomers and/or diastereoisomers, tautomeric forms, salts and metal and metalloid complexes of compounds of formula I as previously defined.

Another variant of the present invention relates to a process for preparing 3-hydroxypicolinic acid derivatives of general formula (I) as defined above and for which:

Y is chosen from a hydrogen atom, a halogen atom, a hydroxyl, mercapto, nitro, thiocyanato, azido, cyano or pentafluorosulfonyl radical, an alkyl, haloalkyl, alkoxy, haloalkoxy, alkylthio, haloalkylthio, alkoxyalkyl, haloalkoxyalkyl, alkylthioalkyl, haloalkylthioalkyl, alkylsulfinyl, haloalkylsulfinyl, alkylsulfonyl, haloalkylsulfonyl or alkoxysulfonyl radical, an amino group, and an N-alkylamino, N,N-dialkylamino, —NHCOR$_{10}$, —NHCSR$_{10}$, N-arylamino, N,N-diarylamino, arylcarbonylamino, arylthiocarbonylamino, aryloxythiocarbonylamino or N,N-arylalkylaminothiocarbonylamino group, the other substituents being as defined above, as well as the optional N-oxides, geometrical and/or optical isomers, enantiomers and/or diastereoisomers, tautomeric forms, salts and metal and metalloid complexes of compounds of formula I as previously defined.

According to yet another variant of the present invention, this invention relates to a process for preparing 3-hydroxypicolinic acid derivatives of general formula (I) as defined above and for which:

Q$_2$ represents a group —NR$_4$R$_5$, in which R$_4$ represents a hydrogen atom and R$_5$ is chosen from an optionally substituted alkyl radical comprising from 1 to 12 carbon atoms in a linear or branched chain, a haloalkyl, alkoxy, haloalkoxy, alkylthio, haloalkylthio, alkenyl or alkynyl radical and a radical chosen from aryl, arylalkyl, heterocyclyl and heterocyclylalkyl, optionally substituted with one or more radicals R$_9$ and/or aryl and/or arylalkyl, which may be identical or different, and/or a group -T-R$_8$, the other substituents being as defined above, as well as the optional N-oxides, geometrical and/or optical isomers, enantiomers and/or diastereoisomers, tautomeric forms, salts and metal and metalloid complexes of compounds of formula (I) as previously defined.

More particularly, the present invention relates to a process for preparing picolinic acid derivatives of general formula (I) as defined above, which have the following characteristics, taken separately or in combination:

X$_1$ and X$_2$ each represent a hydrogen atom,

Z is chosen from an alkyl radical and a hydrogen atom or a cleavable radical capable of donating hydrogen, for example an alkoxyalkyl, haloalkoxyalkyl, alkylthioalkyl, haloalkylthioalkyl, N-alkylaminoalkyl, N,N-dialkylaminoalkyl, acylaminoalkyl, acyl, thioacyl, cyanoalkyl, alkoxythiocarbonyl, N-alkylaminothiocarbonyl, N,N-dialkylaminothiocarbonyl or alkylsulfinyl radical, Y is chosen from a hydrogen atom, a halogen atom, a hydroxyl, mercapto, nitro, thiocyanato, azido, cyano or pentafluorosulfonyl radical, an alkyl, haloalkyl, alkoxy, haloalkoxy, alkylthio, haloalkylthio, alkoxyalkyl, haloalkoxyalkyl, alkylthioalkyl, haloalkylthioalkyl, alkylsulfinyl, haloalkylsulfinyl, alkylsulfonyl, haloalkylsulfonyl or alkoxysulfonyl radical, an amino group, and an N-alkylamino, N,N-dialkylamino, —NHCOR$_{10}$, —NHCSR$_{10}$, N-arylamino, N,N-diarylamino, arylcarbonylamino, arylthiocarbonylamino, aryloxythiocarbonylamino or N,N-arylalkylaminothiocarbonylamino group, Q$_1$ is chosen from an oxygen atom and a sulfur atom, Q$_2$ represents a group —NR$_4$R$_5$, in which R$_4$ represents a hydrogen atom and R$_5$ is chosen from an optionally substituted alkyl radical comprising from 1 to 12 carbon atoms in a linear or branched chain, a haloalkyl, alkoxy, haloalkoxy, alkylthio, haloalkylthio, alkenyl and alkynyl radical and a radical chosen from aryl, arylalkyl, heterocyclyl and heterocyclylalkyl optionally substituted with one or more radicals R$_9$ and/or aryl and/or arylalkyl, which may be identical or different, and/or a group -T-R$_8$, the other substituents being as defined above, as well as the optional N-oxides, geometrical and/or optical isomers, enantiomers and/or diastereoisomers, tautomeric forms, salts and metal and metalloid complexes of compounds of formula (I) as previously defined.

Even more particularly, the present invention relates to a process for preparing 3-hydroxypicolinic acid derivatives of general formula (I) as defined above, which have the flowing characteristics:

X$_1$ and X$_2$ each represent a hydrogen atom,

Z is chosen from an alkyl radical and a hydrogen atom or a cleavable radical capable of donating hydrogen, for example an alkoxyalkyl haloalkoxyalkyl, alkythioalkyl, haloalkylthioalkyl, N-alkylaminoal, N,N-dialkylaminoalkyl, acylaminoalkl,acyl, thioacyl, cyanoalkyl, alkoxythibcarbonyl, N-alkylaminothiocarbonyl, N,N-dialkylaminothiocarbonyl or alkylsulfinyl radical, Y is chosen from a hydrogen atom, a halogen atom, a hydroxyl, mercapto, nitro, thiocyanato, azido, cyano or pentafluorosulfonyl radical, an alkyl, haloalkyl, alkoxy, haloalkoxy, alkylthio, haloalkylthio, alkoxyalkyl, haloalkoxyalkyl, alkylthioalkyl, haloalkylthioalkyl, alkylsulfinyl, haloalkylsulfinyl, alkylsulfonyl, haloalkylsulfonyl or alkoxysulfonyl radical, an amino group, and an N-alkylamino, N,N-dialkylamino, —NHCOR$_{10}$, —NHCSR$_{10}$, N-arylamino, N,N-diarylamino, arylcarbonylamino, arylthiocarbonylamino, aryloxythiocarbonylamino or N,N-arylalkylaminothiocarbonylamino group, Q$_1$ is chosen from an oxygen atom and a sulfur atom, Q$_2$ represents a group —NR$_4$R$_5$, in which R$_4$ represents a hydrogen atom and R$_5$ is chosen from an optionally substituted alkyl radical comprising from 1 to 12 carbon atoms in a linear or branched chain, a haloalkyl, alkoxy, haloalkoxy, alkylthio, haloalkylthio, alkenyl and alkynyl radical and a radical chosen from aryl, arylalkyl, heterocyclyl and heterocyclylalkyl, optionally substituted with one or more radicals $R_9$ and/or aryl and/or arylalkyl, which may be identical or different, and/or a group -T-$R_8$, the other substituents being as defined above, as well as the optional N-oxides, geometrical and/or optical isomers, enantiomers and/or diastereoisomers, tautomeric forms, salts and metal and metalloid complexes of compounds of formula (I) as previously defined.

Even more specifically, the present invention relates to a process for preparing 3-hydroxypicolinic acid derivatives of general formula (I) as defined above, which have the following characteristics:

$X_1$ and $X_2$ each represent a hydrogen atom,

Z is chosen from an alkyl radical and a hydrogen atom or a cleavable radical capable of donating hydrogen, for example an alkoxyalkyl, haloalkoxyalkyl, alkylthioalkyl, haloalkylthioalkyl, N-alkylaminoalkyl, N,N-dialkylaminoalkyl, acylaminoalkyl, acyl, thioacyl, cyanoalkyl, alkoxythiocarbonyl, N-alkylaminothiocarbonyl, N,N-dialkylaminothiocarbonyl or alkylsulfinyl radical, Y is chosen from a hydrogen atom, a halogen atom, a hydroxyl, azido, alkoxy, alkylthio and alkylsulfonyl radical and an amino, —NHCOR$_{10}$ and —NHCSR$_{10}$ group, $Q_1$ represents an oxygen atom, $Q_2$ represents a group —NR$_4$R$_5$, in which $R_4$ represents a hydrogen atom and $R_5$ is chosen from an aryl, arylalkyl, heterocyclyl and heterocyclylalkyl radical, optionally substituted with one or more radicals $R_9$ and/or aryl and/or arylalkyl, which may be identical or different, and/or a group -T-$R_8$, the other substituents being as defined above, as well as the optional N-oxides, geometrical and/or optical isomers, enantiomers and/or diastereoisomers, tautomeric forms, salts and metal and metalloid complexes of compounds of formula (I) as previously defined.

In the context of the present invention, the term "aryl" means phenyl or naphthyl, the term "arylalkyl" means phenylalkyl or naphthylalkyl, more particularly benzyl, plenethyl, phenylpropyl, phenylbuty, naphhthylethyl, naphthylpropyl or naphthylbutyl. It is understood that these various radicals may optionally be substituted with one or more radicals $R_9$ and/or aryl and/or arylalkyl radicals, which may be identical or different.

The terms "heterocyclyl" and "heterocyclylal" are defined similarly, it being understood that "heterocycle" means saturated, partially unsaturated or unsaturated monocycle or bicycle containing from 4 to 10 ring units, comprising at least one hetero atom chosen from nitrogen, oxygen, sulfur, silicon and phosphorus.

More particularly, the term "heterocycle" is understood as being one of the rings (i) to (v) below:

a 5-membered ring; described by formula (i):

(i)

in which each of the groups of the list $B^1, B^2, B^3, B^4$ is chosen from carbon, nitrogen, oxygen and sulfur atoms such that the said list comprises from 0 to 3 carbon atoms, from 0 to 1 sulfur atom, from 0 to 1 oxygen atom and from 0 to 4 nitrogen atoms;

a 6-membered ring described by formula (ii):

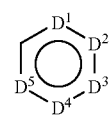

(ii)

in which each of the groups of the list $D^1, D^2, D^3, D^4, D^5$ is chosen from carbon and nitrogen atoms such that the said list comprises from 1 to 4 carbon atoms and from 1 to 4 nitrogen atoms;

two fused rings, each being 6-membered, described by formula (iii):

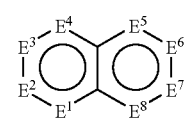

(iii)

in which each of the groups in the list $E^1, E^2, E^3, E^4, E^5, E^6, E^7, E^8$ is chosen from carbon and nitrogen atoms such that the said list comprises from 4 to 7 carbon atoms and from 1 to 4 nitrogen atoms;

a 6-membered ring and a 5-membered ring fused together, described by formula (iv):

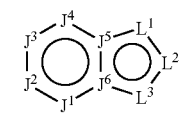

(iv)

in which:
each of the groups in the list $J^1, J^2, J^3, J^4, J^5, J_6$ is chosen from carbon and nitrogen atoms such that the said list comprises from 3 to 6 carbon atoms and from 0 to 3 nitrogen atoms; and each of the groups in the list L1, L2, L3 is chosen from carbon, nitrogen, oxygen and sulfur atoms such that the said list comprises from 0 to 3 carbon atoms, from 0 to 1 sulfur atom, from 0 to 1 oxygen atom and from 0 to 3 nitrogen atoms; and each of the groups in the list $J^1, J^2, J^3, J^4, J^5, J^6, L^1, L^2, L^3$ is chosen such that the said list comprises from 3 to 8 carbon atoms;

two fused rings, each being 5-membered, described by formula (v):

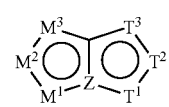

(v)

in which:
each of the groups in the list $M^1, M^2, M^3$ represents, carbon, nitrogen, oxygen or sulfur atoms such that the said list comprises from 0 to 3 carbon atoms, from 0 to 1 sulfur atom, from 0 to 1 oxygen atom and from 0 to 3 nitrogen atoms;

each of the groups in the list $T^1$, $T^2$, $T^3$ represents carbon, nitrogen, oxygen or sulfur atoms such that the said list comprises from 0 to 3 carbon atoms, from 0 to 1 sulfur atom, from 0 to 1 oxygen atom and from 0 to 3 nitrogen atoms;

Z represents a carbon or nitrogen atom;

each of the groups in the list $M^1$, $M^2$, $M^3$, $T^1$, $T^2$, $T^3$ is chosen such that the said list comprises from 0 to 6 carbon atoms.

In the present invention, the term "heterocycle" even more particularly means: furyl, pyrolyl, thienyl, pyrazolyl, imidazolyl, oxazolyl, isoxazolyl, thiazolyl, isothiazolyl, 1,2,3-oxadiazolyl, 1,2,4-oxadiazolyl, 1,2,5-oxadiazolyl, 1,3,4-oxadiazolyl, 1,2,3-thiadiazolyl, 1,2,4-thiadiazolyl, 1,2,5-thiadiazolyl, 1,3,4-thiadiazolyl, 1,2,3-triazolyl, 1,2,4-triazolyl, tetrazolyl, pyridyl, pyrimidinyl, pyrazinyl, pyridazinyl, 1,2,3-triazinyl, 1,2,4-triazinyl, 1,3,5-triazinyl, 1,2,3,4-tetrazinyl, 1,2,3,5-tetrazinyl, 1,2,4,5-tetrazinyl, benzimidazolyl, indazolyl, benzotriazolyl, benzoxazolyl, 1,2-benzisoxazolyl, 2,1-benzisoxazolyl, benzothiazolyl, 1,2-benzisothiazolyl, 2,1-benzisothiazolyl, 1,2,3-benzoxadiazolyl, 2,5-benzoxadiazolyl, 1,2,3-benzothiadiazolyl, 1,2,5-benzothiadiazolyl, quinolyl, isoquinolyl, quinoxazolinyl, quinazolinyl, cinnolyl or phthalazyl, pteridinyl, benzotriazinyl, 1,5-naphthyridinyl, 1,6-naphthyridinyl, 1,7-naphthyridinyl, 1,8-naphthyridinyl, imidazo[2,1-b]thiazolyl, thieno[3,4-b]pyridyl, purine or pyrrolo[1,2-b]thiazolyl.

The present invention most particularly relates to a process for preparing 3-hydroxypicolinic acid derivatives of general formula (I) as defined above, which are:

3-hydroxy-N-{[3-(trifluoromethyl)benzyl]oxy}-2-pyridinecarboxamide,

1-{3-hydroxy-2-[(4-phenoxyanilino)carbonyl]-4-pyridinyl}-1,2-triazadien-2-ium, 4-amino-3-hydroxy-N-{4-[4-(trifluoromethyl)-phenoxy]-phenyl}-2-pyridinecarboxamide, 4-amino-3-hydroxy-N-[4-(4-methylphenoxy)phenyl]-2-pyridinecarboxamide, 4-(formylamino)-3-hydroxy-N-{4-[3-(trifluoromethyl)-phenoxy]phenyl}-2-pyridinecarboxamide, N-[4-(4-chlorophenoxy)phenyl]-4-(formylamino)-3-hydroxy-2-pyridinecarboxamide, 4-(formylamino)-3-hydroxy-N-{4-[4-(trifluoromethyl)-phenoxy]phenyl}-2-pyridinecarboxamide and N-[4-(benzyloxy)phenyl]-4-(formylamino)-3-hydroxy-2-pyridinecarboxamide, as well as the optional N-oxides, geometrical and/or optical isomers, enantiomers and/or diastereoisomers, tautomeric forms, salts and metal and metalloid complexes thereof.

The compounds of general formula (I) and the compounds which may be used as intermediates in the processes of preparation, and which will be defined in the description of these processes, can exist in one or more forms of geometrical isomers according to the number of double bonds in the compound. The compounds of general formula (I) where $Q_1$ is —$NR_1$ or —N—$NR_4R_5$ can comprise 2 different geometrical isomers denoted (E) or (Z) depending on the configuration of the two double bonds. The E and Z notation can be replaced, respectively, by the term syn and anti, or cis and trans. Reference is made particularly to the work of E. Eliel and S. Wilen "Stereochemistry of Organic Compound", published by Wiley (1994), for the description and use of these notations.

The compounds of general formula (I) and compounds which may be used as intermediates in the processes of preparation, and which will be defined in the description of the processes, can exist in one or more optical isomeric or chiral forms according to the number of asymmetric centres in the compound. The invention thus also relates to all the optical isomers and their racemic or scalemic (scalemic designates a mixture of enantiomers in different proportions), as well as the mixtures of all possible stereoisomers in all proportions. The separation of the diastereoisomers and/or optical isomers can be effected by known methods (E. Eliel ibid.).

The present invention thus relates to the process of preparation of the compounds of general formula (I) and compounds useful as intermediates in the processes of preparation, described in a general way below. Although general, this method of preparation provides all of the operating conditions to be used for the synthesis of the compounds of formula (I) according to the present invention. It will nevertheless be understood that the skilled worker will be able to adapt this method according to the specifics of each of the compounds which it is desired to synthesize.

The preparation of reagents used in one or other of the general methods of preparation is generally known and is generally described specifically in the prior art or in such a manner that the man skilled in the art can adapt it to the desired aim. The prior art usable by the normally skilled worker in order to establish conditions for the preparation of reagents can be found in numerous general chemistry text books such "Advanced Organic Chemistry" by J. March, published by Wiley (1992), "Methoden der organischen Chemie" (Houben-Weyl), published by Georg Thieme Verlag, or the "Chemical Abstracts" published by the American Chemical Society as well as in information data bases accessible to the public.

The compounds of general formula (I) may advantageously be prepared from a compound of formula (II) (described, for example, in patent U.S. Pat. No. 5,652,363):

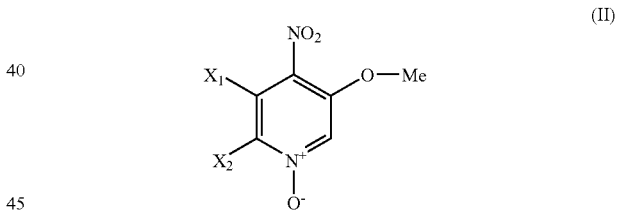

in which $X_1$ and $X_2$ are as defined above, which compound is placed in contact with a cyanide, alkali metal derivatives or alkaline-earth metal derivatives of hydrocyanic acid in the presence of an alkylating agent and a solvent, or with trimethylsilyl cyanide in the presence of dimethylcarbamoyl chloride and a solvent, to give the compounds of formula (III)

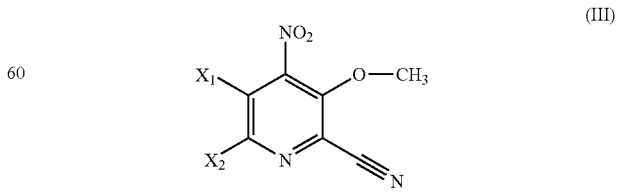

in which $X_1$ and $X_2$ are as defined above.

The compounds of formula (III) above can be converted into corresponding halo derivatives of formula (IVa)

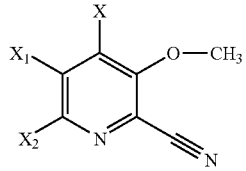
(IVa)

in which $X_1$ and $X_2$ are as defined above and X represents a halogen atom chosen from fluorine, chlorine, bromine and iodine, by reaction with an acyl halide in the presence of a solvent, such as, preferably, but not exclusively, an ethereal solvent such as diethyl ether, diisopropyl ether, tetrahyrofuran, dioxane or 1,2-dimethoxyethane.

The halo derivatives of formula (IVa) are then hydrolyzed into compounds of formula (Ia):

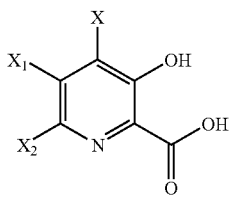
(Ia)

in which X, $X_1$ and $X_2$ are as defined above, by the action of a hot hydracid—or a strong mineral base, optionally in the presence of aqueous hydrogen peroxide solution—and optionally boron tribromide as described in the abovementioned publications.

One variant which is possible for this hydrolysis reaction consists in treating the nitrile of formula (IVa) with an acid, in particular hydrochloric acid, hydroiodic acid or hydrobromic acid, or alkylsulfonic acids, this hydrolysis reaction being carried out in excess acid, in the absence or presence of a solvent, at reflux or at a temperature of between 20° C. and 200° C.

The compounds of formula (III) or (IVa) may also be placed in contact with an alcohol or an alkoxide in the presence of a solvent such as, preferably, but not exclusively, a protic or polar aprotic solvent, to give the compounds of formula (IVb)

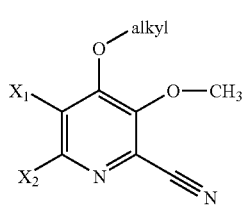
(IVb)

in which $X_1$ and $X_2$ are defined above, and may then be used in a hydrolysis reaction under operating conditions similar to those used for the formation of the compounds of formula (Ia), to give the compounds of the 6 respective formulae (Ib) and (Ib'):

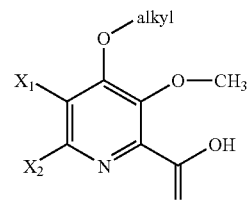
(Ib)

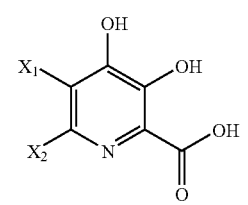
(Ib')

in which $X_1$ and $X_2$ are as defined above.

The compounds of formula (IVa) may also be converted into picolinic acid derivatives of formula (Va): in which $X_1$, $X_2$ and $R_6$ are as defined above, by reacting a compound of formula $R_6SH$, or a corresponding alkali metal or alkaline-earth metal salt, in an aprotic polar solvent, such as dimethylformamide, dimethylacetamide, N-methylpyrrolidone, dimethylpropyleneurea or dimethyl sulfoxide, at a temperature between 0° C. and the boiling point of the solvent. The nitrites of formula (Va) may then be used in a hydrolysis reaction to give the corresponding acids of formula (Ic): in which $X_1$, $X_2$ and $R_6$ are as defined above, according to a reaction similar to the one used for the formation of the compounds of formula (Ia).

The halides of formula (IVa) may also be treated with an azothydric acid salt, more particularly with sodium azide, to give the compounds of formula (Vb): in which $X_1$ and $X_2$ are as defined above, this reaction preferably being carried out in a polar aprotic solvent such as dimethylformamide, dimethylacetamide, N-methylpyrrolidone, dimethylpropyleneurea or dimethyl sulfoxide, at a temperature between 0° C. and the boiling point of the solvent.

The compounds of formula (Vb) may then be hydrolyzed according to techniques similar to those presented for the preparation of the acids of formula (Ia) above, to give the acids of formula (Id):

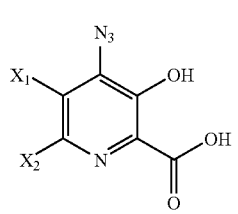
(Id)

in which $X_1$ and $X_2$ are as defined above.

The azides of formula (Id) are then optionally reduced to amine derivatives of formula (Ie):

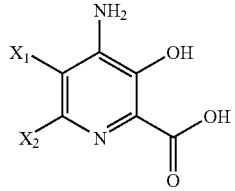

(Ie)

in which $X_1$ and $X_2$ are as defined above, by the action of reducing agents such as, for example, lithium aluminum hydride, triphenylphosphine or hydrogen in the presence of a catalyst, or alternatively any other reducing agent as described by J. March, *ibid*, p. 1219-1220.

The acids of formulae (Ia) to (Ie) can be converted into thio acids, imino derivatives (—C(=NR$_1$)) or amino imino derivatives (—C(=N—NR$_4$R$_5$)) according to standard techniques that are well known to those skilled in the art specialized in organic synthesis.

Similarly, the acids (Ia) and (Ie), or the thio, imino and imino amino derivatives thereof defined above, substituted in position 3 (relative to the pyridine nitrogen atom) with —OH or -methoxy may be subjected to various reactions that are already known in the prior art, in order to give the corresponding derivatives substituted in position 3 (relative to the pyridine nitrogen atom) with —O-Z, Z being as defined for the compounds of formula (I).

The compounds of formula (I) defined above for which Y represents an amino (—NH$_2$) radical may be placed in contact with an acylating agent in the presence of a solvent and optionally of a base. The term acylating agent preferentially means, but in a non-limiting manner, an acyl halide, an anhydride, an acid, an ester or a primary amide, and the thio-homologs thereof, as described in J. March, *ibid*, pages 417-424, to give the compounds of formulae (VIa) and (VIb):

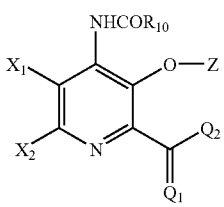

(VIa)

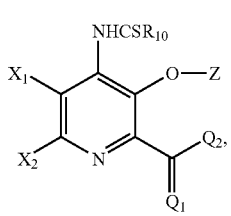

(VIb)

in which $X_1$, $X_2$, $Q_1$, $Q_2$, Z and $R_{10}$ are as defined above.

The picolinic acid derivatives of formula (VII):

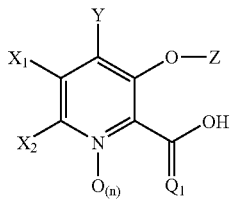

(VII)

in which $X_1$, $X_2$, $Q_1$, n, Z and Y are as defined above, may be placed in contact with a reagent of formula $R_2$OH, $R_3$SH or HNR$_4$R$_5$, $R_2$, $R_3$, $R_4$ and $R_5$ being as defined above, to give the compounds of formulae (VIIIa), (VIIIb) and (VIIIc), respectively, forming the set of compounds of formulae (VIII):

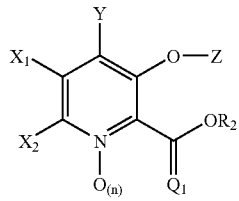

(VIIIa)

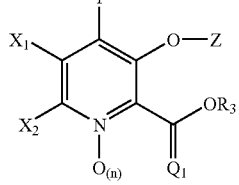

(VIIIb)

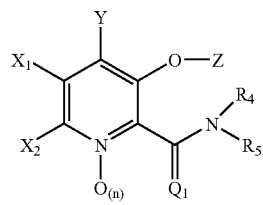

(VIIIc)

which are special cases of the compounds of formula (I) in which $Q_2$ represents —OR$_2$, —SR$_3$ and —NR$_4$R$_5$, respectively.

The above reaction is carried out in the presence of an activating agent such as thionyl chloride, oxalyl chloride, dicyclocarbodiimide, 1-(3-dimethylaminopropyl)-3-ethyl-carbodiimide hydrochloride, 1-hydroxybenzotriazole or phosphorus oxichloride or the like, as described in the reference publications, in the presence of organic or inorganic base, in the absence or presence of a solvent. These reagents may, where appropriate, be linked to a polymer resin.

The reaction is generally carried out at a temperature of between −80 °C. and 180°C. (preferably between 0°C. and 150°C.) or at the boiling point of the solvent used. The solvent which is suitable for this reaction may be an aliphatic hydrocarbon such as pentane, hexane, heptane or octane, an aromatic hydrocarbon such as benzene, toluene, xylene or halobenzenes, an ether such as diethyl ether, diisopropyl ether, tetrahydrofuran, dioxane or dimethoxyethane, a halogenated hydrocarbon such as dichloromethane, chloroform, 1,2-dichloroethane or 1,1,1-trichloroethane, an ester such as methyl acetate or ethyl acetate, a nitrile such as acetonitrile, propionitrile or benzonitrile, or a polar aprotic solvent such as dimethylformamide, dimethylacetamide, N-methylpyrrolidone, dimethylpropyleneurea, dimethyl sulfoxide, pyridine or water. Mixtures of these various solvents may also be used.

The reaction time depends on the conditions used and is generally between 0.1 h and 48 h. As organic or inorganic bases that are suitable for this reaction, mention may be made of alkali metal hydroxides and alkali-earth metal hydroxides such as sodium hydroxide potassium hydroxide, cesium hydroxide or calcium hydroxide, alkali metal alkoxides and alkaline-earth metal alkoxides such as potassium tert-butoxide, alkali metal hydrides and alkaline-earth metal hydrides, such as sodium, hydride, potassium hydride or cesium hydride, alkali metal carbonates and bicarbonates or alkaline-earth metal carbonates and bicarbonates, such as sodium carbonate, potassium carbonate, calcium carbonate or sodium bicarbonate, potassium bicarbonate or calcium bicarbonate, organic bases, preferably organonitrogen bases, such as pyridine, alkylpyridines, alkylamines such as trimethylamine, triethylamine or diisopropylethylamine, and aza derivatives such as 1,5-diazabicylco[4.3.0]non-5-ene or 1,8-diazabicylco[5.4.0]undec-7-ene.

The reaction may be carried out using an excess of a base which is liquid at the reaction temperature, this base then also acting as solvent. Mention may be made of organonitrogen bases such as pyridine or alkylpyridines.

There is no strict limitation on the relative proportions of the compounds of formula (VII) and of formula (VIII). However, it is advantageous to select a (VIII)/(VII) molar ratio of between 0.1 and 10, preferably 0.5 to 2.

The compounds of general formula (XI):

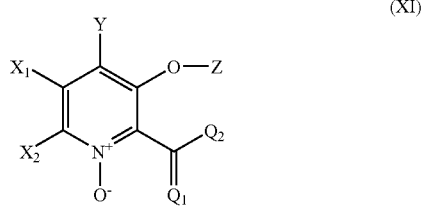

(XI)

which are special cases of the compounds of formula (I) for which n is equal to 1, may be obtained by a process which consists in placing a compound of formula (X):

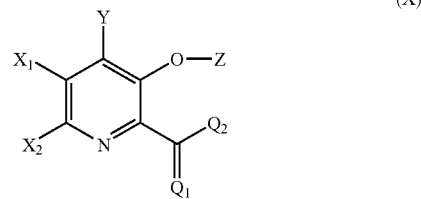

(X)

which is a special case of the compounds of formula (I) for which n is equal to zero, in contact with an oxidizing agent as described in J. March, ibid., page 1200, in particular aqueous hydrogen peroxide solution or carboxylic, boronic or sulfuric peracids.

It should be understood that the reactions described in the preceding paragraphs may be carried out in any other order which is suitable to obtain the desired compounds of formula (I). The order of the reactions will be determined most particularly by the compatibility requirements of the various substituents on the pyridine nucleus. The compatibilities of the various radicals and reagents used are well known to the person skilled in the art, who may moreover refer to the examples for the preparation of the compounds of formula (I) described later in this description.

The 3-hydroxypicolinic acid derivatives of formula (I) described in the present invention are useful in the agrochemical field and in human and animal therapy. Specifically, 3-hydroxypicolinic acid derivatives of formula (I) have advantageous antifungal properties enabling them to effectively combat fungal diseases of crops and also fungal diseases encountered in man and animals. The large antifungal potential of the compounds of formula (I) also allows them to be used in any field for which it is required and/or necessary to combat microscopic fungi such as, for example, molds.

The following examples illustrate in a non-limiting manner several examples of fungicidal compounds according to the invention. In the examples which follow, "MP" signifies "melting point" and is expressed ° Celsius (° C.).

EXAMPLE a

Preparation of 2cyano-3-methoxy-4-nitropyridine

A mixture of 12.5 g (12.5 moles) of the N-oxide of 3 methoxy-4-nitropyridine, 7.72 ml (1.1 eq.) of methyl sulfate and 70 ml of 1,2-dichloroethane is heated at 70° C. for 2.5 hours. It is allowed to cool and 70 ml of water are added. It is cooled in a salt and ice bath and, in portions, 7.55 g (2.1 moles) of sodium cyanide are added, controlling the temperature so as not to exceed 10° C. After 4 hours stirring, the reaction mixture is extracted with ethyl ether, the organic phase is washed with water, concentrated and the residue chromatographed (ethyl acetate/dichloromethane). There is obtained 7.06 g of a yellow oil (yield 53%).

EXAMPLE b

Preparation of 4-bromo-2-cyano-3-methoxypyridine

A mixture of 6 g (0.0335 moles) of 2-cyano-3-methoxy-4-nitropyridine obtained in Example a), 12.37 g (0.100 moles) of acetyl bromide and 36 ml of 1,2-dimethoxyethane is heated at 85° C. for 1.5 hours. It is allowed to cool and the reaction mixture is poured onto 100 g of crushed ice. 30 ml of 1,2-dichloroethane are added and gently neutralized to pH=8 with a 28% aqueous solution of ammonia. After extraction with 1,2-dichloroethane, washing with water, drying and concentration the residue is chromatographed (ethyl acetate/heptane, 3:7) to obtain 5.32 g (75% yield) of a white solid (MP=116° C.).

In a similar manner, replacing the acetyl bromide by acetyl chloride, there is obtained 4-chloro-2-cyano-3-methoxpyridine (83% yield) in the form of a white solid (MP=91° C.).

EXAMPLE c

Preparation of 4-azido-2-cyano-3-methoxypyridine

To 1 g (0.0155 moles) of sodium azide in 25 ml of dimethylformamide at 0° C., there is added gently 3 g (0.0141 moles) of 4-bromo-2-cyano-3-methoxypyridine from Example b), dissolved in 40 ml of dimethylformamide. The mixture is stirred for 6 hours at ambient temperature. The reaction mixture is diluted in 200 ml of iced water and extracted with dichloromethane. The organic phase is washed twice with water, dried, concentrated and the residue chromatographed (ethyl acetate/heptane, 3:7). There is obtained 0.87 g (35% yield) of a white solid (MP=102° C.).

EXAMPLE d

Preparation of 4-chloro-3-hydroxypicolinic Acid

A mixture of 2 g (0.012 moles) of 4-chloro-2-cyano-3-methoxypyridine obtained in Example b), and 7 ml of 37% hydrochloric acid is heated at 100° C. for 12 hours. After cooling the solid formed is filtered, washed once with water and 3 times with acetone and dried under vacuum for 8 hours. There is obtained 1.78 g (86% yield) of a yellow solid (MP=228° C.).

In the same manner, the following hydroxy acids are obtained:

| Y | Hydracid | Yield, MP (° C.) |
|---|---|---|
| 4-bromo-3-hydroxy-picolinic acid | HBr | Yellow solid, 82%, 230° C. |
| 4-azido-3-hydroxy-picolinic acid | HCl | Violet solid, 63% |
| 3,4-dihydroxypicolinic acid | HBr | White solid, 74%, 264° C. |

EXAMPLE e

Preparation of 2-cyano-3,4-dimethoxypyridine 3 g (0.017 moles) of 2-cyano-3-methoxy-4-nitropyridine obtained in Example a) and a sodium methoxide solution prepared from 0.77 g (0.033 moles) of sodium and 65 ml of methanol are stirred at ambient temperature for 4 hours. There is added 100 ml of water, the methanol is eliminated and the aqueous phase is extracted with dichloromethane. The organic phase is washed with water, dried, concentrated and the residue chromatographed (ethyl acetate/heptane, 1:1) to obtain 1.96 g (72% yield) of a white solid (MP=133° C.).

EXAMPLE f

Preparation of 2-cyano-3-hydroxy-4-thiomethoxypyridine 2 g of 4-bromo-2-cyano-3-methoxypyridine obtained in Example b) and 2.16 g of sodium thiomethoxide in 40 ml of anhydrous dimethylformamide are heated at 85° C. for 5 hours. After cooling and the addition of 20 ml of water, the reaction mixture is concentrated to dryness. The residue is extracted three times with hot methanol. The cooled methanolic phase is filtered and concentrated. There is obtained 1.51 g (97% yield) of a brown syrup used crude.

EXAMPLE g

Preparation of 3-hydroxy-4-thiomethoxypicolinic acid 2.5 g (0.015 moles) of 2-cyano-3-hydroxy-4-thiomethoxy-pyridine from Example f), 8.5 g of potassium hydroxide and 25 ml of water are heated at reflux for 2.5 hours. After allowing to cool and in an ice bath the mixture is gently neutralized with 1N hydrochloric acid to pH=2-3. The solid formed is filtered. The solid is washed once with water and three times with acetone; it is dried under vacuum for 8 hours. There is obtained 1.81 g (68% yield) of a white solid (MP=247° C.).

EXAMPLE h

Preparation of 3,4-dimethoxypicolinic acid 1 g of 3,4-dimethoxy-2-cyanopyridine obtained in Example e) and 3.5 g of potassium hydroxide in 15 ml of water are heated to 85° C. for half an hour. It is allowed to cool and in an ice bath hydrochloric acid is added gently to pH=2-3. After concentration to dryness, the residue is extracted three times with hot methanol, allowed to cool, filtered and concentrated. There is obtained a solid used crude.

EXAMPLE i

Preparation of the N-oxide of 3-hydroxypicolinic acid

To a mixture of 20 ml acetic acid and 20 ml of hydrogen peroxide solution, are added 2 g of 3-hydroxypicolinic acid; the whole is heated at 80° C. for 5 hours. After elimination of the solvents under vacuum, the solid obtained is washed with hot alcohol to obtain 2.02 g of compound in the form of a white solid (MP=182° C.).

EXAMPLE 1

3-Hydroxy-4-methoxy-N-para-phenoxyphenylpicolinamide 0.046 g of para-phenoxyaniline, 0.04 g of 3-hydroxy-4-methoxypicolinic acid (obtained in a manner similar to that described in Example g)), 0.034 g of 1-hydroxybenzotriazole and 0.060 g of 1-(3-dimethylaminopropyl)-3-ethylcarbodi-imide hydrochloride are heated in 2 ml of pyridine between 75 and 85° C. for 1 to 2 hours. After cooling, the residue is taken up in a mixture of dichloromethane and 2 mL of 1N hydrochloric acid. After extraction with dichloromethane, concentration and chromatography on silica there is obtained 0.057 g of the title compound, a yellow solid (MP=186° C.).

EXAMPLE 2

4-amino-3-hydroxy-N-para-phenoxyphenylpicolinamide

To 0.14 g of 4-azido-3-hydroxy-N-para-phenoxyphenylpi-colinamide (obtained from the compound of Example 1 according to the methods described in Examples a) to g)) dissolved in a mixture of ethanol/ethyl acetate, 1:2, there is added a spatula tip of 10% palladium on carbon. Hydrogenation is carried out at 20 bars pressure and ambient temperature for 4-5 hours. After filtration, concentration and chromatography of the residue in ethyl acetate, there is obtained 0.099 g of a white solid (MP:197° C.).

EXAMPLE 3

4-formamido-3-hydroxy-N-para-phenoxyphenylpi-colinamide

There is heated at reflux 61.2 mg of acetic anhydride and 27.6 mg of formic acid for 4 hours and 46 mg of 4-amino-3-hydroxy-N-para-phenoxyphenylpicolin-amide of Example 2 is added, dissolved in 5 ml of tetrahydrofuran. After 8 hours at reflux, the reaction mixture is concentrated and purified by chromatography to give 39 mg of a yellow solid MP 208° C.

The compounds described in the following Tables 1 and 2 are prepared in a similar manner:

TABLE 1

| N° | Q2 | O—Z | Y | MP |
|---|---|---|---|---|
| 4 | NH—C6H4—O—C6H5 (4-phenoxyanilino, attached via gem-dimethyl) | OH | H | 114 |
| 5 | benzyloxy-phenyl-NH- (via gem-dimethyl) | HO | H | 151 |
| 6 | 2,5-dimethoxy-4-(benzamido)-anilino-X | OH | H | 250 |
| 7 | 2-methyl-5-methoxy-4-(benzamido)-anilino-X | OH | H | 234 |
| 8 | 4-(4-chlorophenoxy)-phenyl-NH- (via gem-dimethyl) | OH | H | 108 |

TABLE 1-continued
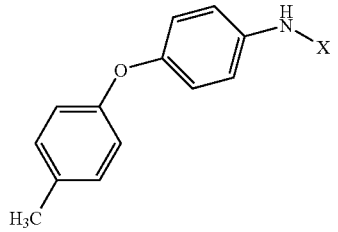
| N° | Q2 | O—Z | Y | MP |
|---|---|---|---|---|
| 9 | 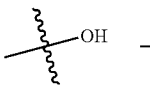 |  OH | 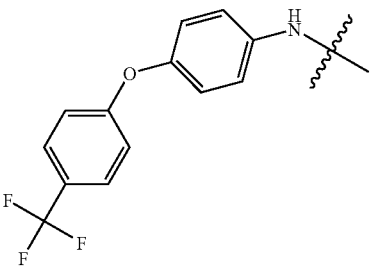 H | 98 |
| 10 | 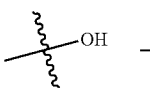 |  OH | 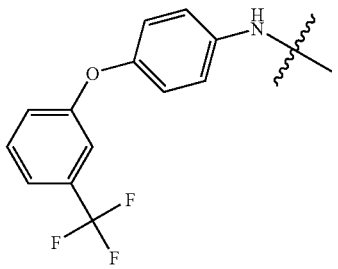 H | 144 |
| 11 | 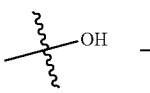 |  OH | 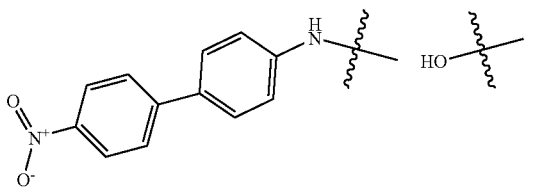 H | 116 |
| 12 | 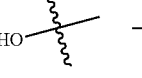 | HO  | 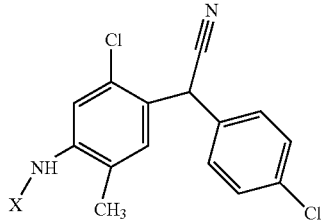 H | 260 |
| 13 |  |  OH | H | 186 |

TABLE 1-continued

| N° | Q2 | O—Z | Y | MP |
|---|---|---|---|---|
| 14 | 2-Cl, 5-(NH-X), 4-CH₃, N-benzoyl aniline | OH | H | 238 |
| 15 | 4-(NH-X)-N-isopropyl-N-phenyl aniline | OH | H | 260 |
| 16 | 3-nitrobenzyl-O-NH- | HO | H | 165 |
| 17 | 4-cyanobenzyl-O-NH- | HO | H | 178 |
| 18 | 2-cyanobenzyl-O-NH- | HO | H | 120 |
| 19 | 3-methoxybenzyl-O-NH-X | HO | H | 62 |

TABLE 1-continued

| N° | Q2 | O—Z | Y | MP |
|---|---|---|---|---|
| 20 | 2,6-di(sec-butyl)phenoxy-phenyl-NH-X | OH | H | 72 |
| 21 | 3-cyanobenzyl-O-NH- | OH | H | 124 |
| 22 | 2-methylbenzyl-O-NH-X | OH | H | 76 |
| 23 | 5-chlorothiophen-2-yl-methyl-O-NH- | OH | H | 128 |
| 24 | 3-trifluoromethylbenzyl-O-NH- | OH | H | 86 |
| 25 | 2-phenoxyethyl-O-NH- | OH | H | 1.58* |

TABLE 1-continued
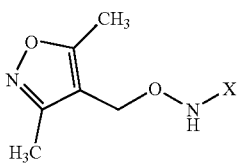
| N° | Q2 | O—Z | Y | MP |
|---|---|---|---|---|
| 26 | 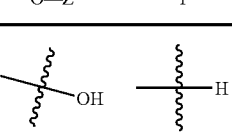 | 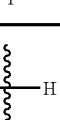OH | 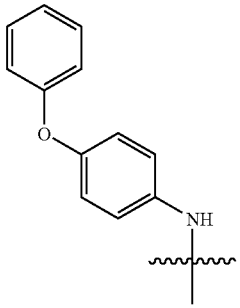H | 138 |
| 27 | 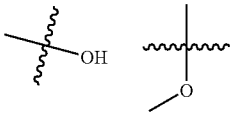 | 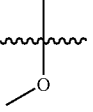OH | 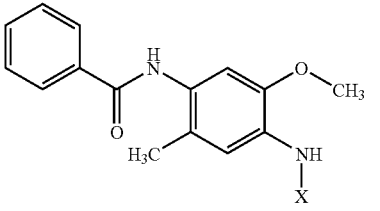 | 186 |
| 28 | 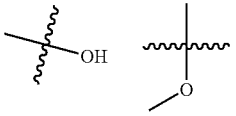 | 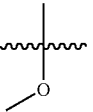OH | 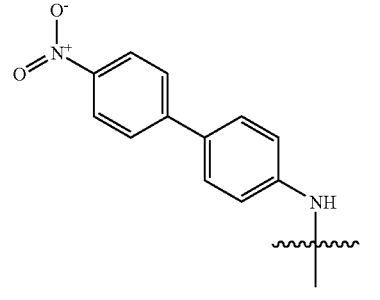 | |
| 29 | 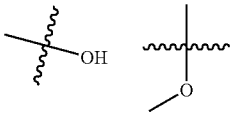 | 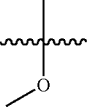OH | 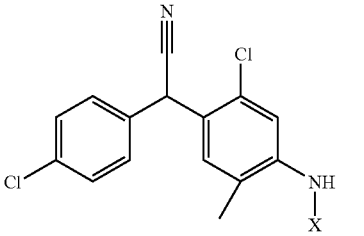 | |
| 30 | 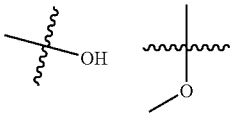 | 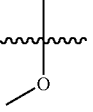OH | | |

TABLE 1-continued

| N° | Q2 | O—Z | Y | MP |
|---|---|---|---|---|
| 31 | (benzamide with Cl, CH3, NHX substituents on phenyl) | OH | OMe | |
| 32 | (triphenyl-substituted aniline) | OH | OMe | 122 |
| 33 | (dimethoxy phenylsulfonamide with NHX) | OH | OMe | 162 |
| 34 | (4'-fluoro-biphenyl-4-amine) | OH | OMe | 248 |

TABLE 1-continued
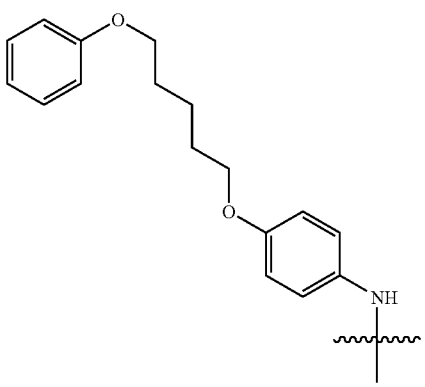
| N° | Q2 | O—Z | Y | MP |
|---|---|---|---|---|
| 35 | 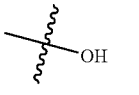 | —OH | —O— | |
| 36 | 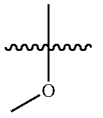 | —OH | —O— | 174 |
| 37 | 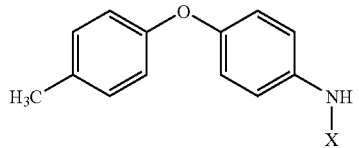 | —OH | —O— | 161 |
| 38 | 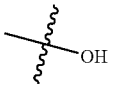 | —OH | —O— | 144 |
| 39 | 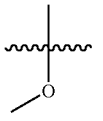 | —OH | —O— | 170 |

TABLE 1-continued
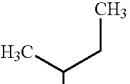
| N° | Q2 | O—Z | Y | MP |
|---|---|---|---|---|
| 40 | 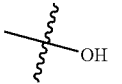 | OH | 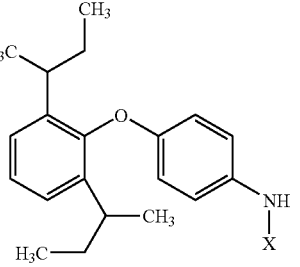 | 182 |
| 41 | 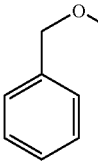 | 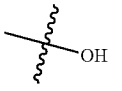OH |  | 162 |
| 42 | 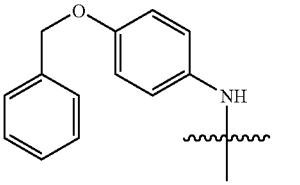 | OH | 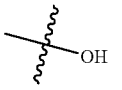 | 210 |
| 43 |  | 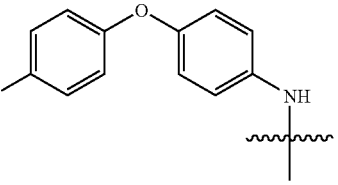OH | 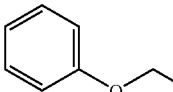 | 158 |
| 44 | 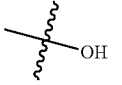 | OH | 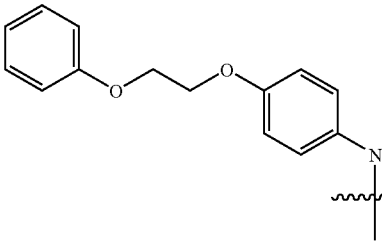 | 140 |
| 45 | 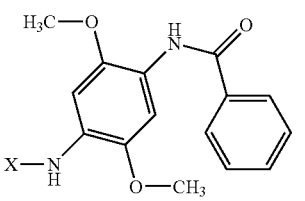 | HO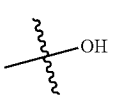 | Br | 140 |

TABLE 1-continued

| N° | Q2 | O—Z | Y | MP |
|---|---|---|---|---|
| 46 | 3,5-bis(trifluoromethyl)phenyl-NH— | —OH | —H | 159 |
| 47 | 2-chlorophenyl-NH— | —OH | —H | 116 |
| 48 | 3-chlorophenyl-NH— | —OH | —H | 134 |
| 49 | 4-chlorophenyl-NH— | —OH | —H | 138 |
| 50 | 4-(pyridin-2-ylcarbamoyl)phenyl-NH— | —OH | —OCH₃ | |
| 51 | 3,5-bis(trifluoromethyl)phenyl-NH— | —OH | —OCH₃ | |

TABLE 1-continued
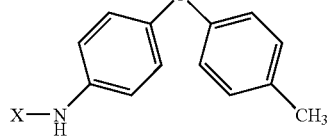
| N° | Q2 | O—Z | Y | MP |
|---|---|---|---|---|
| 52 |  |  OH | 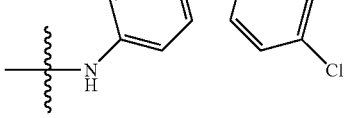 Br | 168 |
| 53 | 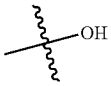 |  OH | 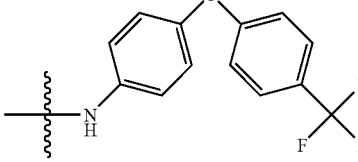 Br | 155 |
| 54 | 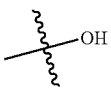 |  OH | 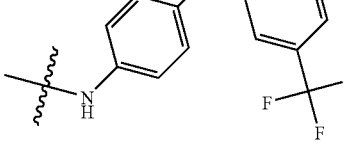 Br | 145 |
| 55 | 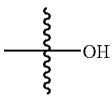 |  OH | 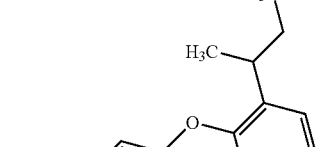 Br | 118 |
| 56 | 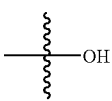 |  OH | 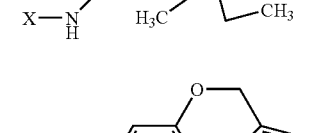 Br | 86 |
| 57 |  |  OH | Br | 165 |

TABLE 1-continued

| N° | Q2 | O—Z | Y | MP |
|----|----|-----|---|-----|
| 58 | 2,5-dimethoxy-4-(X-NH)-phenyl benzamide | OH | Br | 250 |
| 59 | 2-methyl-5-methoxy-4-(X-NH)-phenyl benzamide | OH | Br | 255 |
| 60 | 2-chloro-5-methyl-4-(X-NH)-phenyl benzamide | OH | Br | 235 |
| 61 | 2-chloro-6-methyl-4-(X-NH)-phenyl (6-chloropyridin-3-yl)acetonitrile | OH | Br | 162 |
| 62 | 4'-nitro-biphenyl-4-yl-NH— | OH | Br | 292 |

TABLE 1-continued

| N° | Q2 | O—Z | Y | MP |
|---|---|---|---|---|
| 63 | (2,5-dimethoxy-4-(X-NH)phenyl)sulfonyl-N-phenyl | —OH | Br | 168 |
| 64 | (2,4,6-triphenylphenyl)NH— | —OH | Br | 135 |
| 65 | 4-(4-hydroxyphenoxy)phenyl-NH— | —OH | Br | 165 |
| 66 | 4-chlorophenyl-NH— | —OH | Br | 161 |
| 67 | 4-(2-phenoxyethoxy)phenyl-NH— | —OH | Br | 160 |

TABLE 1-continued

| N° | Q2 | O—Z | Y | MP |
|---|---|---|---|---|
| 68 | (4-phenoxybutoxy-phenyl)amino group | OH | Br | 122 |
| 69 | (4-(phenylcarbamoyl)phenyl)amino group | OH | Br | 256 |
| 70 | (4-(4-methylphenoxy)phenyl)amino, X—NH | OH | S-Me | 198 |
| 71 | (4-(4-trifluoromethylphenoxy)phenyl)amino | OH | S-Me | 162 |
| 72 | (4-(3-trifluoromethylphenoxy)phenyl)amino | OH | S-Me | 139 |

TABLE 1-continued

| N° | Q2 | O—Z | Y | MP |
|---|---|---|---|---|
| 73 | (4-sec-butyl-2-(sec-butyl)phenoxy)phenyl-NH— attached via X—NH | —OH | —S—CH₃ | 150 |
| 74 | 4-(benzyloxy)phenyl-NH— attached via X—NH | —OH | —S—CH₃ | 208 |
| 75 | 2,5-dimethoxy-4-(benzamido)phenyl-NH— attached via X—NH | —OH | —S—CH₃ | 210 |
| 76 | 2-methyl-5-methoxy-4-(benzamido)phenyl-NH— attached via X—NH | —OH | —S—CH₃ | 242 |
| 77 | 2-chloro-5-methyl-4-(benzamido)phenyl-NH— attached via X—NH | —OH | —S—CH₃ | 243 |

TABLE 1-continued
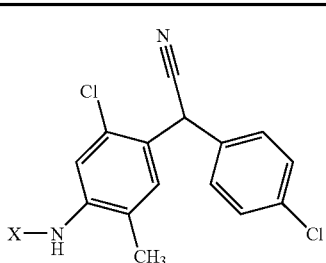
| N° | Q2 | O—Z | Y | MP |
|---|---|---|---|---|
| 78 |  | 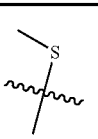 | 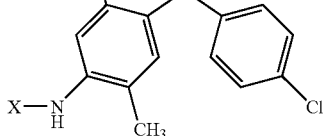 | 212 |
| 79 | 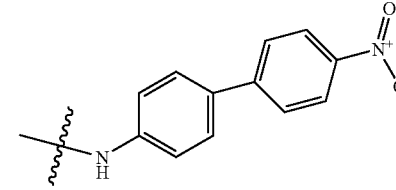 |  |  | |
| 80 | 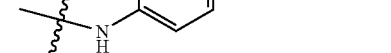 | 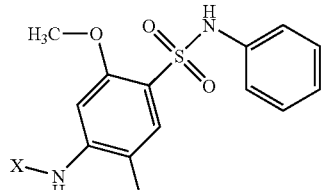 |  | 185 |
| 81 |  | 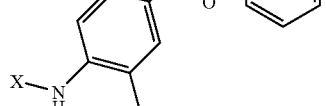 | 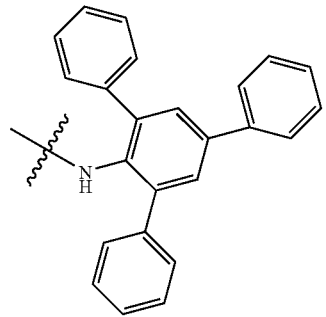 | 118 |
| 82 |  |  | 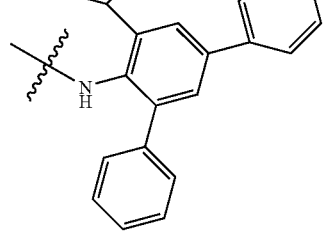 | 172 |

TABLE 1-continued

| N° | Q2 | O—Z | Y | MP |
|---|---|---|---|---|
| 83 | 4-Cl-C6H4-NH- | -OH | -S-CH3 | 214 |
| 84 | 4-(2-phenoxyethoxy)-C6H4-NH- | -OH | -S-CH3 | 172 |
| 85 | 4-(4-phenoxybutoxy)-C6H4-NH- (X—NH) | -OH | -S-CH3 | 122 |
| 86 | 4-(phenylcarbamoyl)-C6H4-NH- | -OH | -S-CH3 | 248 |
| 87 | 3,5-bis(trifluoromethyl)-C6H3-NH- | -OH | -S-CH3 | 168 |

TABLE 1-continued

| N° | Q2 | O—Z | Y | MP |
|---|---|---|---|---|
| 88 | 4-phenoxyphenyl-NH- | -OH | -S-CH₃ | 186 |
| 89 | 4-phenoxyphenyl-NH- | -OH | -Cl | 120 |
| 90 | 4-(4-methylphenoxy)phenyl-NH(X)- | -OH | -Cl | 146 |
| 91 | 4-(4-chlorophenoxy)phenyl-NH- | -OH | -Cl | 148 |

TABLE 1-continued
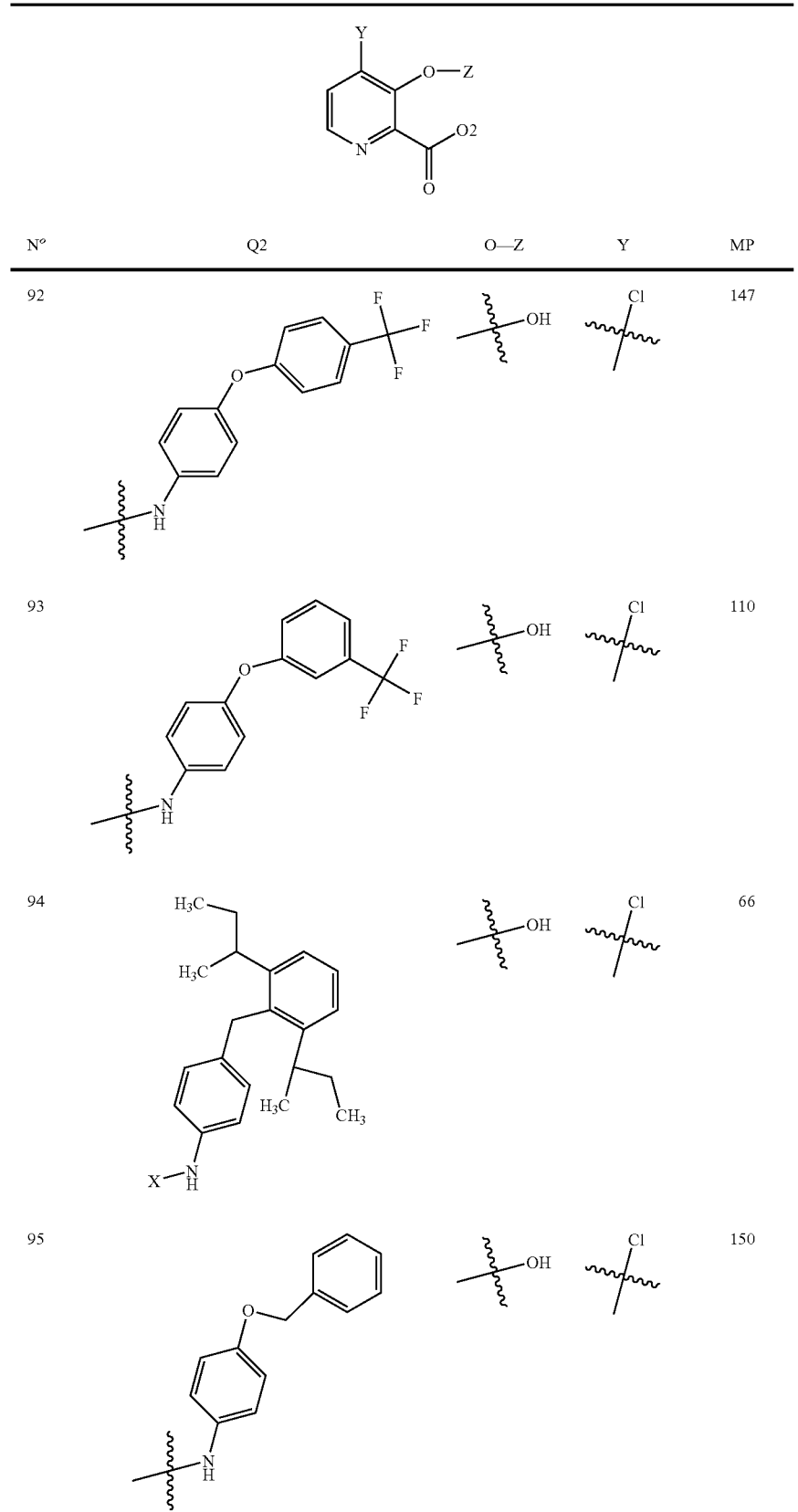
| N° | Q2 | O—Z | Y | MP |
|---|---|---|---|---|
| 92 | 4-(4-(trifluoromethyl)phenoxy)phenyl-NH— | —OH | Cl | 147 |
| 93 | 4-(3-(trifluoromethyl)phenoxy)phenyl-NH— | —OH | Cl | 110 |
| 94 | 4-(2,6-di-sec-butylbenzyl)phenyl-NH—X | —OH | Cl | 66 |
| 95 | 4-(benzyloxy)phenyl-NH— | —OH | Cl | 150 |

TABLE 1-continued

| N° | Q2 | O—Z | Y | MP |
|---|---|---|---|---|
| 96 | 2,5-dimethoxy-4-(X-NH)-phenyl-NH-C(O)-phenyl | —OH | Cl | 246 |
| 97 | 2-methyl-5-methoxy-4-(X-NH)-phenyl-NH-C(O)-phenyl | —OH | Cl | 260 |
| 98 | 2-chloro-5-methyl-4-(X-NH)-phenyl-NH-C(O)-phenyl | —OH | Cl | 226 |
| 99 | 2-chloro-5-methyl-4-(X-NH)-phenyl-C(CN)(4-chlorophenyl) | —OH | Cl | 140 |
| 100 | X-NH-(4-(4-nitrophenyl)phenyl) | —OH | Cl | 166 |
| 101 | 2,5-dimethoxy-4-(X-NH)-phenyl-SO2-NH-phenyl | —OH | Cl | 166 |

TABLE 1-continued

| N° | Q2 | O—Z | Y | MP |
|---|---|---|---|---|
| 102 | (2,6-diphenyl-4-phenylphenyl)NH— | —C(CH₃)₂OH | Cl | 124 |
| 103 | (3-chlorophenyl)NH— | —C(CH₃)₂OH | Cl | 174 |
| 104 | (4-chlorophenyl)NH— | —C(CH₃)₂OH | Cl | 166 |
| 105 | (2-chlorophenyl)NH— | —C(CH₃)₂OH | Cl | 164 |
| 106 | [4-(4-phenoxybutoxy)phenyl]NH— | —C(CH₃)₂OH | Cl | 120 |

TABLE 1-continued

| N° | Q2 | O—Z | Y | MP |
|----|----|----|---|----|
| 107 | phenyl-NH-C(=O)-C6H4-NH- | -OH | Cl | 279 |
| 108 | 3,5-bis(trifluoromethyl)phenyl-NH- | -OH | Cl | 76 |
| 109 | 4-(2-phenoxyethoxy)phenyl-NH- | -OH | Cl | 156 |
| 110 | 4-phenoxyphenyl-NH- | -OH | OH | 284 |
| 111 | 4-(4-methylphenoxy)phenyl-NH- | -OH | OH | 265 |

TABLE 1-continued
| N° | Q2 | O—Z | Y | MP |
|---|---|---|---|---|
| 112 | 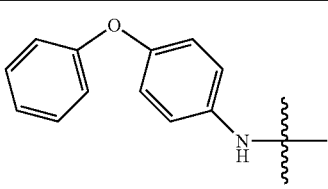 | 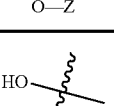 | 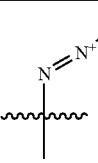 | 138 |
| 113 | 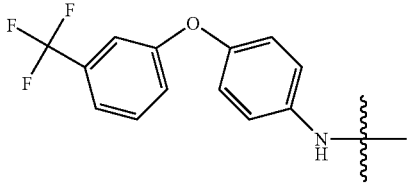 | 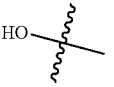 | 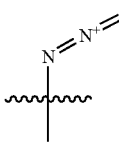 | |
| 114 | 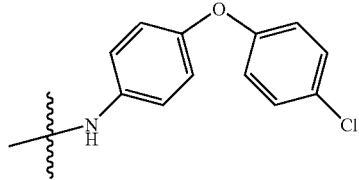 | 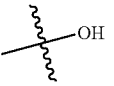 |  | 271 |
| 115 | 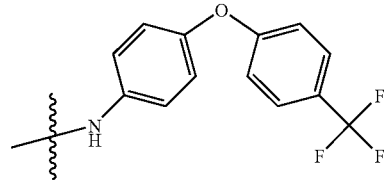 | 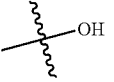 |  | 274 |
| 116 | 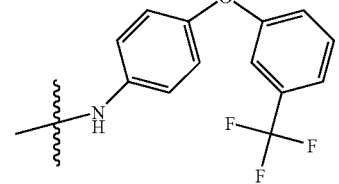 | 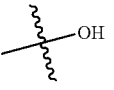 |  | 252 |
| 117 | 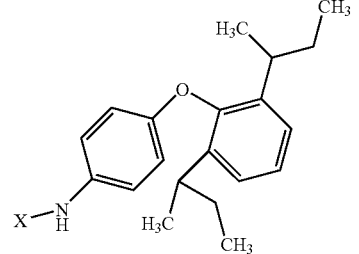 | 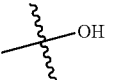 |  | 272 |

TABLE 1-continued

| N° | Q2 | O—Z | Y | MP |
|---|---|---|---|---|
| 118 | 4-benzyloxyphenyl-NH– | –OH | OH | 294 |
| 119 | 2,5-dimethoxy-4-(benzoylamino)phenyl-NH(X) | –OH | OH | 296 |
| 120 | 2-methyl-5-methoxy-4-(benzoylamino)phenyl-NH(X) | –OH | OH | — |
| 121 | 4-phenoxyphenyl-NH– | –OCH₃ | OCH₃ | 108 |
| 122 | 4-(4-methylphenoxy)phenyl-NH(X) | –OCH₃ | OCH₃ | 106 |
| 123 | 4-(4-chlorophenoxy)phenyl-NH– | –OCH₃ | OCH₃ | thick oil |

TABLE 1-continued

| N° | Q2 | O—Z | Y | MP |
|---|---|---|---|---|
| 124 | 4-(4-(trifluoromethyl)phenoxy)phenyl-NH— | —O-CH₃ | —O-CH₃ | 89 |
| 125 | 4-(3-(trifluoromethyl)phenoxy)phenyl-NH— | —O-CH₃ | —O-CH₃ | 92 |
| 126 | 2,6-di(sec-butyl)-4-phenoxyphenyl-NH—X | —O-CH₃ | —O-CH₃ | — |
| 127 | 4-(benzyloxy)phenyl-NH— | —O-CH₃ | —O-CH₃ | thick oil |
| 128 | 2,5-dimethoxy-4-(benzamido)phenyl-NH—X | —O-CH₃ | —O-CH₃ | 132 |

TABLE 1-continued
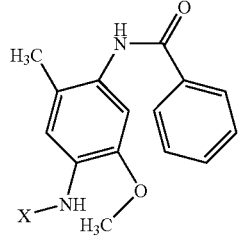
| N° | Q2 | O—Z | Y | MP |
|---|---|---|---|---|
| 129 | 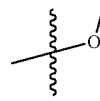 |  | 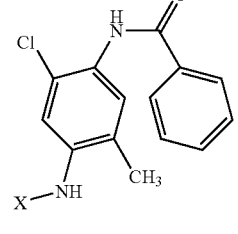 | 254 |
| 130 | 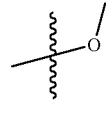 |  | 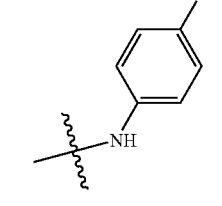 | 212 |
| 131 | 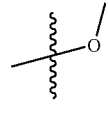 |  | 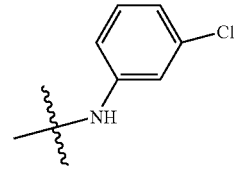 | 121 |
| 132 | 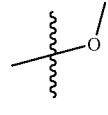 |  | 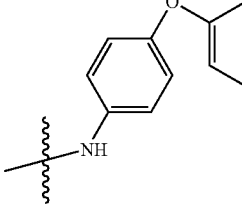 | thick oil |
| 133 |  |  | 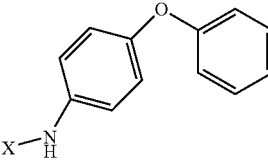 | thick oil |
| 134 | 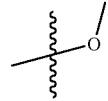 |  | | 102 |

TABLE 1-continued

| N° | Q2 | O—Z | Y | MP |
|---|---|---|---|---|
| 135 | 4-(4-chlorophenoxy)phenylamino | —O—CH₃ | —S— | 114 |
| 136 | 4-(2,6-di-sec-butylphenoxy)phenylamino | —O—CH₃ | —S— | — |
| 137 | 4-(3-trifluoromethylphenoxy)phenylamino | —O—CH₃ | —S— | 136 |
| 138 | 4-phenoxyphenylamino | —OH | —NH₂ | 197 |
| 139 | 4-(3-trifluoromethylphenoxy)phenylamino | —OH | —NH₂ | 199 |

TABLE 1-continued

| N° | Q2 | O—Z | Y | MP |
|---|---|---|---|---|
| 140 | (2-Cl, 5-methyl, 4-NHX-phenyl)-NH-C(=O)-phenyl | —OH | OH | |
| 141 | (2-Cl, 5-methyl, 4-NHX-phenyl)-CH(CN)-(4-Cl-phenyl) | —OH | OH | 148 |
| 142 | 4'-nitro-biphenyl-4-yl-NH— | —OH | OH | |
| 143 | (3-Cl-phenyl)-NH— | —OH | OH | 277 |
| 144 | (4-Cl-phenyl)-NH— | —OH | OH | 288 |

TABLE 1-continued

| N° | Q2 | O—Z | Y | MP |
|---|---|---|---|---|
| 145 | 3,5-bis(trifluoromethyl)phenyl-NH- | -C(OH)< | -OH | 278 |
| 146 | 4-(PhNHC(O))-phenyl-NH- | -C(OH)< | -OH | — |
| 147 | 4-(2-phenoxyethoxy)phenyl-NH- | -C(OH)< | -OH | 276 |
| 148 | 2-fluorophenyl-NH- | -C(OH)< | -OMe | 187 |
| 149 | 4-bromophenyl-NH- | -C(OH)< | -OMe | 227 |
| 150 | 4-iodophenyl-NH- | -C(OH)< | -OMe | 260 |

TABLE 1-continued

| N° | Q2 | O—Z | Y | MP |
|---|---|---|---|---|
| 151 | 4-ethoxyphenyl-NH- | OH | OMe | 152 |
| 152 | 4-trifluoromethoxyphenyl-NH- | OH | OMe | 205 |
| 153 | benzo[1,3]dioxol-5-ylmethyl-NH- | OH | OMe | 161 |
| 154 | 4-butoxyphenyl-NH- | OH | OMe | 148 |
| 155 | 3-methylphenyl-NH- | OH | OMe | 137 |
| 156 | 3-chlorophenyl-NH- | OH | OMe | 165 |

TABLE 1-continued

| N° | Q2 | O—Z | Y | MP |
|---|---|---|---|---|
| 157 | 3-nitro-phenyl-NH- | -OH | -OCH₃ | 248 |
| 158 | 3-trifluoromethyl-phenyl-NH- | -OH | -OCH₃ | 154 |
| 159 | 4-fluoro-phenyl-NH- | -OH | -OCH₃ | 178 |
| 160 | 2-ethyl-phenyl-NHX- | -OH | -OCH₃ | 148 |
| 161 | 2-methoxy-phenyl-NHX- | -OH | -OCH₃ | 135 |
| 162 | 3-(methylthio)-phenyl-NHX- | -OH | -OCH₃ | 169 |

TABLE 1-continued
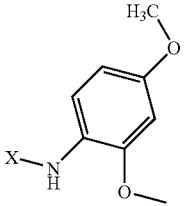
| N° | Q2 | O—Z | Y | MP |
|---|---|---|---|---|
| 163 | 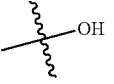 |  —OH | 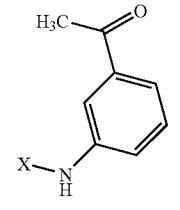 | 130 |
| 164 | 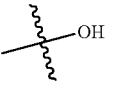 |  —OH | 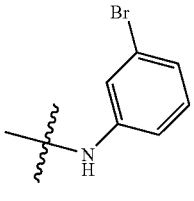 | 185 |
| 165 | 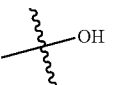 |  —OH | 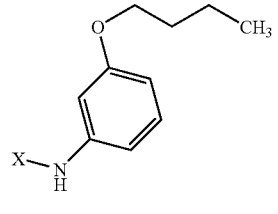 | 187 |
| 166 | 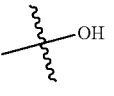 |  —OH | 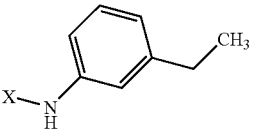 | 162 |
| 167 | 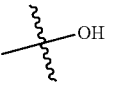 |  —OH | 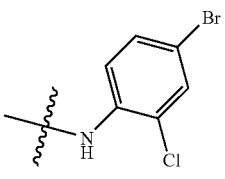 | 144 |
| 168 | 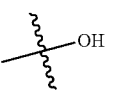 |  —OH | | 154 |

TABLE 1-continued

| N° | Q2 | O—Z | Y | MP |
|----|----|----|---|----|
| 169 | 3-cyanophenyl-NH- | -C(CH3)2-OH | -O-C(CH3)2- | 192 |
| 170 | 4-(4-methylphenoxy)phenyl-NH-X | -C(CH3)2-OH | -N3 | 121 |
| 171 | 4-(4-chlorophenoxy)phenyl-NH- | -C(CH3)2-OH | -N3 | 113 |
| 172 | 4-(4-trifluoromethylphenoxy)phenyl-NH- | -C(CH3)2-OH | -N3 | 105 |
| 173 | 4-(2,6-di-sec-butylphenoxy)phenyl-NH-X | -C(CH3)2-OH | -N3 | 106 |
| 174 | 4-benzyloxyphenyl-NH- | -C(CH3)2-OH | -N3 | 135 |

TABLE 1-continued

| N° | Q2 | O—Z | Y | MP |
|---|---|---|---|---|
| 175 | 3-(trifluoromethyl)benzyl-NH- | -OH | -O- | 138 |
| 176 | 4-methoxybenzyl-NH-X | -OH | -O- | 113 |
| 177 | benzyl-NH- | -OH | -O- | 131 |
| 178 | 2-acetylphenyl-NH- | -OH | -O- | 171 |
| 179 | 2-(trifluoromethyl)phenyl-NH- | -OH | -O- | 165 |
| 180 | 2,4-dibromophenyl-NH- | -OH | -O- | 175 |
| 181 | 4-phenoxyphenyl-NH- | -OH | -S(=O)$_2$- | |

TABLE 1-continued
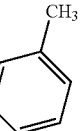
| N° | Q2 | O—Z | Y | MP |
|---|---|---|---|---|
| 182 | 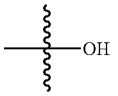 | 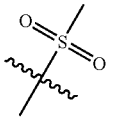 —OH | 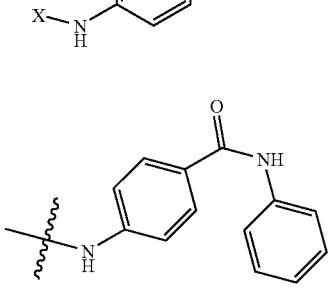 | |
| 183 | 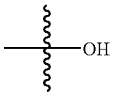 | 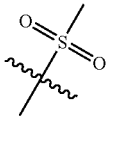 —OH | 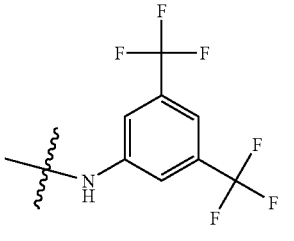 | |
| 184 | 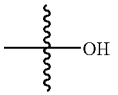 | 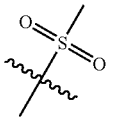 —OH | 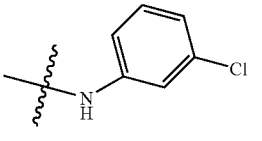 | 170 |
| 185 | 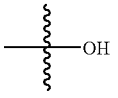 | 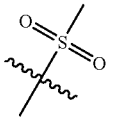 —OH | 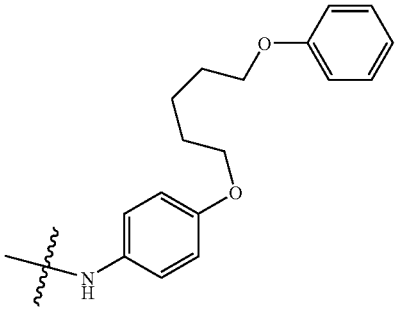 | 142 |
| 186 | 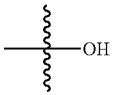 | 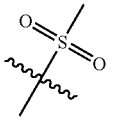 —OH | | |

TABLE 1-continued
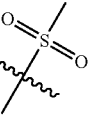
| N° | Q2 | O—Z | Y | MP |
|---|---|---|---|---|
| 187 | 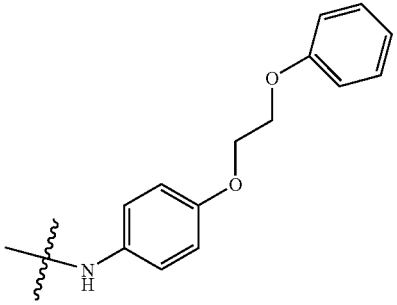 | 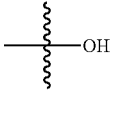 | 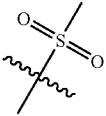 | |
| 188 | 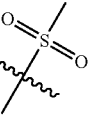 | 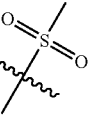 | 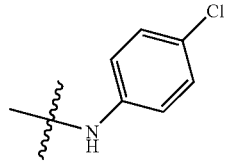 | |
| 189 | 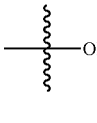 | 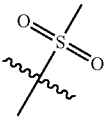 | 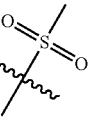 | |
| 190 | 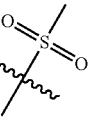 | 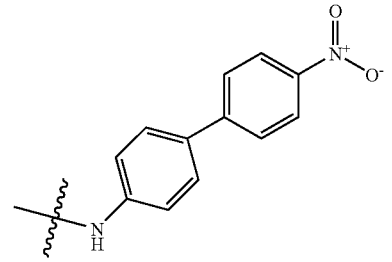 | 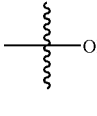 | |
| 191 | 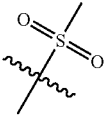 | 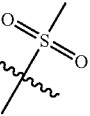 | 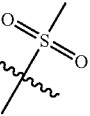 | |

TABLE 1-continued

| N° | Q2 | O—Z | Y | MP |
|---|---|---|---|---|
| 192 | (2,5-dimethoxy-4-(X-NH)phenyl)benzamide | —OH | methylsulfonyl | |
| 193 | 4-(benzyloxy)phenyl-NH— | —OH | methylsulfonyl | |
| 194 | 4-(2,6-di-sec-butylphenoxy)phenyl-NH-X | —OH | methylsulfonyl | 117 |
| 195 | 4-(4-(trifluoromethyl)phenoxy)phenyl-NH— | —OH | methylsulfonyl | |
| 196 | 4-(benzyloxy)phenyl-NH— | —OH | NH$_2$ | 214 |

TABLE 1-continued

| N° | Q2 | O—Z | Y | MP |
|---|---|---|---|---|
| 197 | 4-(4-chlorophenoxy)phenylamino | OH | NH₂ | 252 |
| 198 | 4-(4-trifluoromethylphenoxy)phenylamino | OH | NH₂ | 232 |
| 199 | 4-(2,6-di-sec-butylphenoxy)phenylamino | | NH₂ | 246 |
| 200 | 4-(4-methylphenoxy)phenylamino | OH | NH₂ | 227 |
| 201 | 4-phenoxyphenylamino | OH | NHCHO | 208 |
| 202 | 4-(3-trifluoromethylphenoxy)phenylamino | OH | NHCHO | 208 |

TABLE 1-continued
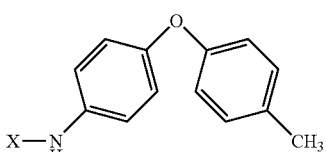
| N° | Q2 | O—Z | Y | MP |
|---|---|---|---|---|
| 203 |  | 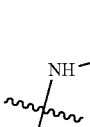 |  | 185 |
| 204 |  | 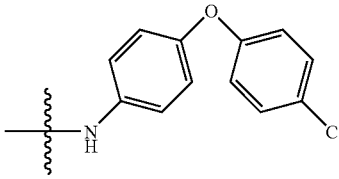 | 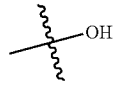 | 198 |
| 205 | 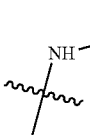 |  |  | 173 |
| 206 | 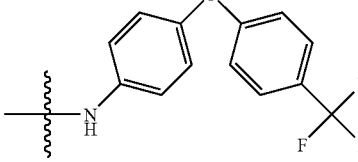 | 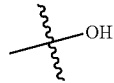 | 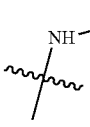 | 170 |
| 207 |  |  | 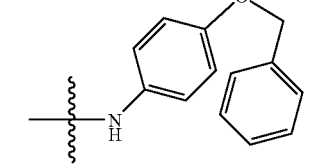 | 143 |
| 208 |  | 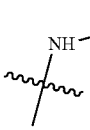 |  | 230 |

TABLE 1-continued
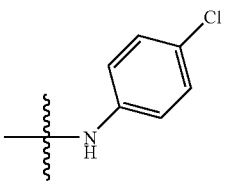
| N° | Q2 | O—Z | Y | MP |
|---|---|---|---|---|
| 209 |  | 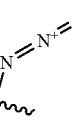 | 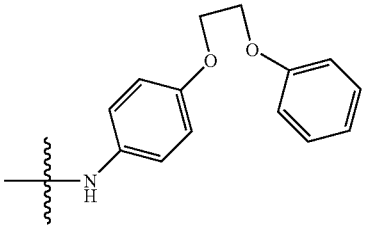 | 128 |
| 210 |  | 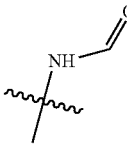 | 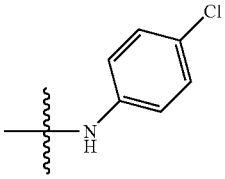 | 232 |
| 211 |  |  | 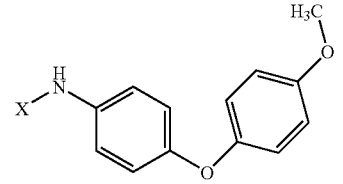 | AS90328 |
| 212 |  |  | 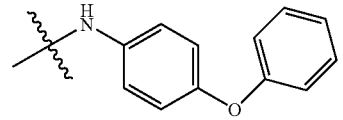 | 230 |
| 213 |  | 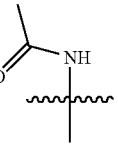 | 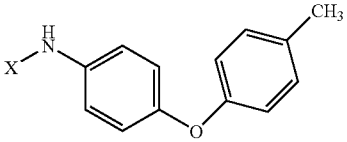 | |
| 214 |  | 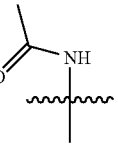 | 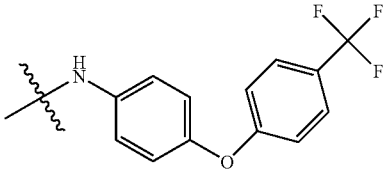 | |
| 215 |  | 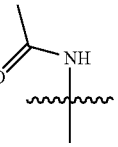 | | |

TABLE 1-continued
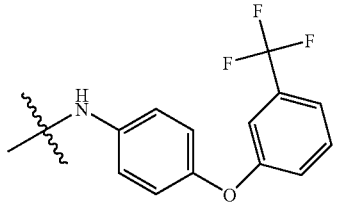
| N° | Q2 | O—Z | Y | MP |
|---|---|---|---|---|
| 216 | 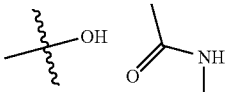 | 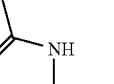—OH | 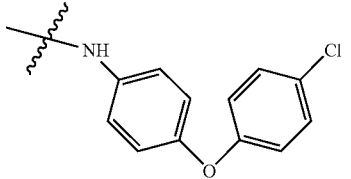 | |
TABLE 2
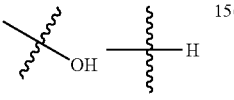
| N° | Q2 | O—Z | Y | MP |
|---|---|---|---|---|
| 217 | 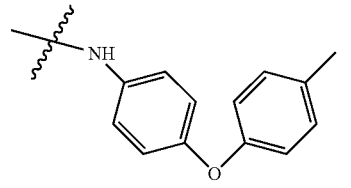 | —OH | H | 156 |
| 218 | 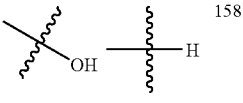 | —OH | H | 158 |
| 219 | 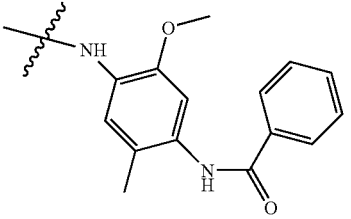 | —OH | H | 258 |

TABLE 2-continued
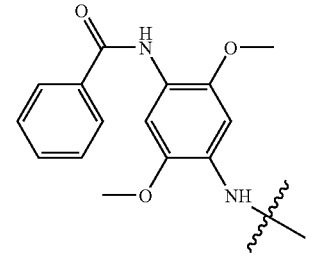
| N° | Q2 | O—Z | Y | MP |
|---|---|---|---|---|
| 220 | 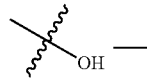 |  OH | H | 244 |
| 221 | 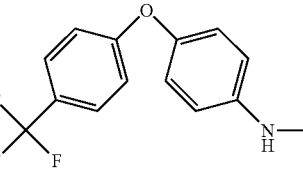 | HO  | H | 156 |
| 222 |  | HO 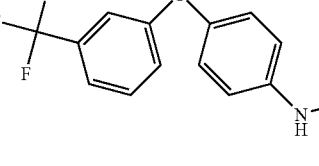 | H | 150 |
| 223 |  | HO  | H | 156 |
| 224 | 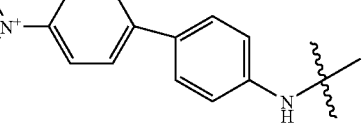 | HO  | H | 275 |
| 225 |  | HO 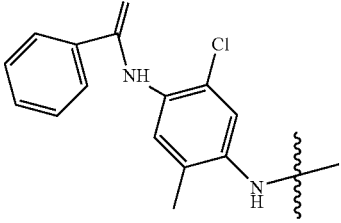 | H | 178 |

TABLE 2-continued

[Structure: pyridine N-oxide with Y at 4-position, O–Z at 3-position, and C(=O)Q2 at 2-position]

| N° | Q2 | O—Z | Y | MP |
|---|---|---|---|---|
| 226 | [4-(benzyloxy)phenyl]amino- | OH | H | 114 |
| 227 | (4-phenoxyphenyl)amino- | OH | H | 128 |
| 228 | [4-(2,6-di-sec-butylphenoxy)phenyl]amino- | OH | H | — |
| 229 | [3,5-bis(trifluoromethyl)phenyl]amino- | OH | H | 176 |
| 230 | (2-chlorophenyl)amino- | OH | H | 178 |

TABLE 2-continued

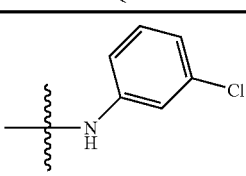

| N° | Q2 | O—Z | Y | MP |
|---|---|---|---|---|
| 231 | 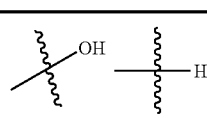 |  | H | 172 |
| 232 | 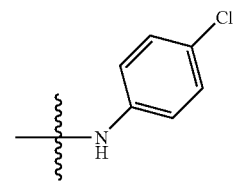 | 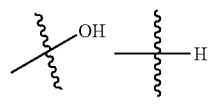 | H | 160 |

EXAMPLES OF BIOLOGICAL ACTIVITY OF THE COMPOUNDS OF THE INVENTION

Example A in vivo Test on *Alternaria Brassicae* (Leaf Spot of Crucifers

An aqueous suspension, with a concentration of 2 g/l, of the active material tested is obtained by grinding it finely in the following mixture:

water

Tween 80 surfactant (polyoxyethylenated derivative of sorbitan oleate) diluted to 10% in water: 5 ml/mg of active material clay: inert support q.s. 100%.

This aqueous suspension is then diluted with water so as to obtain the desired active material concentration.

Radish plants (Pernot variety) in starter cups, sown on a 50/50 peat soil-pozzolana substrate and grown at 18-20° C., are treated at the cotyledon stage by spraying with the aqueous suspension described above.

Plants, used as controls, are treated with an aqueous solution not containing the active material.

After 24 hours, the plants are contaminated by spraying them with an aqueous suspension of *Alternaria brassicae* spores (40,000 spores per cm³). The spores are collected from a 12-13-day-old culture.

The contaminated radish plants are incubated for 6-7 days at about 18° C., under a humid atmosphere.

Grading is carried out 6 to 7 days after the contamination, in comparison with the control plants.

Under these conditions, good (at least 50%) or total protection is observed at a dose of 250 g/ha with the following compounds: 198, 200, 202, 206, 206.

Example B in vivo Test on *Septoria Nodorum* (*Septoria* Disease of Wheat

An aqueous suspension, with a concentration of 2 g/l, of the active material tested is obtained by grinding it finely in the following mixture:

water

Tween 80 surfactant (polyoxyethylenated derivative of sorbitan oleate) diluted to 10% in water: 5 ml/mg of active material clay: inert support q.s. 100%.

This aqueous suspension is then diluted with water so as to obtain the desired active material concentration.

Wheat plants (Scipion variety) in starter cups, sown on a 50/50 peat soil-pozzolana substrate and grown at 12° C., are treated at the 1-leaf stage (10 cm tall) by spraying them with the aqueous suspension described above.

Plants, used as controls, are treated with an aqueous solution not containing the active material.

After 24 hours, the plants are contaminated by spraying with an aqueous suspension of *Septoria nodorum* spores (500,000 spores per cm³). The spores are collected from a seven-day-old culture.

The contaminated wheat plants are incubated for 72 hours at about 18° C., under a humid atmosphere, and then for 14 days at 90% relative humidity.

Grading is carried out 15 to 20 days after contamination, in comparison with the control plants.

Under these conditions, good (at least 50%) or total protection is observed, at a dose of 250 g/ha, with the following compounds: 198, 200, 202.

Example C in vivo Test on *Magnaporthe Grisea* (Blast Disease of Rice

An aqueous suspension, with a concentration of 50 mg/l, of the active material tested is obtained by grinding it finely in the following mixture:
water,
2% acetone.

Rice plants (Koshihirakari variety), sown on Kureha soil and grown in 33 cm² plastic pots up to the 3-4 leaf stage, are treated by spraying with the aqueous suspension described above.

Plants, used as controls, are treated with an aqueous solution not containing active material.

24 hours after treatment, the plants are contaminated by spraying with an aqueous suspension of *Magnaporthe grisea* spores (500,000 spores per cm³).

The contaminated rice plants are placed in an incubator for 24 hours at 25° C. under a humid atmosphere, and then for 5 to 7 days in an incubation chamber at 20-25° C. and 70-90% relative humidity.

Grading is carried out 5 to 7 days after the contamination, by counting the lesions on the first leaf of the plant.

Under these conditions, good (at least 50%) or total protection is observed, at a dose of 50 mg/l, with the following compounds: 24, 112, 204, 205.

The invention claimed is:

1. A process for preparing a 3-hydroxypicolinic acid derivative compound of formula (I):

$$\text{(I)}$$

wherein:
n represents 0 or 1,
$Q_1$ is selected from the group consisting of an oxygen or sulfur atom, a group $NR_1$ and a group $N-NR_4R_5$,
$Q_2$ is selected from the group consisting of a group $OR_2$ or $SR_3$ and a group $-NR_4R_5$, or
$Q_1$ and $Q_2$ may together form a ring of 5 to 7 atoms containing 2 to 3 oxygen and/or nitrogen atoms, optionally substituted with one or more radicals, which may be identical or different, selected from the group consisting of halogens and alkyl and haloalkyl radicals,
Z is selected from the group consisting of a hydrogen atom, a cyano radical and an alkyl, allyl, aryl, arylalkyl, propargyl, cycloalkyl, halocycloalkyl, alkenyl, alkynyl, cyanoalkyl, haloalkyl, alkoxyalkyl, haloalkoxyalkyl, alkylthioalkyl, haloalkylthioalkyl, N-alkylaminoalkyl, N,N-dialkylaminoalkyl, acylaminoalkyl, alkoxycarbonylaminoalkyl, aminocarbonylaminoalkyl, alkoxycarbonyl, N-alkylaminocarbonyl, N,N-dialkylaminocarbonyl, acyl, thioacyl, alkoxythiocarbonyl, N-alkylaminothiocarbonyl, N,N-dialkylaminothiocarbonyl, alkylsulfinyl, haloalkylsulfinyl, alkylsulfonyl, haloalkylsulfonyl, alkoxysulfonyl, aminosulfonyl, N-alkylaminosulfonyl, N,N-dialkylaminosulfonyl, arylsulfinyl, arylsulfonyl, aryloxysulfonyl, N-arylaminosulfonyl, N,N-diarylaminosulfonyl and an N,N-arylalkylaminosulfonyl radical;
Y is selected from the group consisting of a hydrogen atom, a halogen atom, a hydroxyl, mercapto, nitro, thiocyanato, azido, cyano or pentafluorosulfonyl radical, an alkyl, haloalkyl, alkoxy, haloalkoxy, alkylthio, haloalkylthio, alkoxyalkyl, haloalkoxyalkyl, alkylthioalkyl, haloalkylthioalkyl, cyanoalkyl, cyanoalkoxy, cyanoalkylthio, alkylsulfinyl, haloalkylsulfinyl, alkylsulfonyl, haloalkylsulfonyl or alkoxysulfonyl radical, a cycloalkyl, halocycloalkyl, alkenyl, alkynyl, alkenyloxy, alkynyloxy, alkenylthio or alkynylthio group, an amino, N-alkylamino, N,N-dialkylamino, —NHCOR$_{10}$, —NHCSR$_{10}$, N-alkylaminocarbonylamino, N,N-dialkylaminocarbonylamino, aminoalkyl, N-alkylaminoalkyl, N,N-dialkylaminoalkyl, acylaminoalkyl, thioacylamino, alkoxythiocarbonylamino, N-alkylaminothiocarbonylamino, N,N-dialkylaminothiocarbonylamino, N,N-arylalkylaminocarbonylamino, N-alkylsulfinylamino, N-alkylsulfonylamino, N-arylsulfinylamino, N-arylsulfonylamino, N-alkoxysulfonylamino, N-alkoxysulfinylamino, N-haloalkoxysulfinylamino, N-haloalkoxysulfonylamino, N-arylamino, N,N-diarylamino, arylcarbonylamino, alkoxycarbonylamino, N-arylaminocarbonylamino, N,N-diarylaminocarbonylamino, arylthiocarbonylamino, aryloxythiocarbonylamino, N-arylaminothiocarbonylamino, N,N-diarylaminothiocarbonylamino or N,N-arylalkylaminothiocarbonylamino group, an acyl, carboxyl, carbamoyl, N-alkylcarbamoyl, N,N-dialkylcarbamoyl, lower alkoxycarbonyl, N-arylcarbamoyl, N,N-diarylcarbamoyl, aryloxycarbonyl or N,N-arylalkylcarbamoyl group, and an imino group of formula:

$X_1$ and $X_2$ are independently selected from the group consisting of a hydrogen atom, a halogen atom, a hydroxyl, mercapto, nitro, thiocyanato, azido, cyano or pentafluorosulfonyl radical, and an alkyl, haloalkyl, alkoxy, haloalkoxy, alkylthio, haloalkylthio, alkoxyalkyl, haloalkoxyalkyl, alkylthioalkyl, haloalkylthioalkyl, cyanoalkyl, cyanoalkoxy, cyanoalkylthio, alkylsulfinyl, haloalkylsulfinyl, alkylsulfonyl, haloalkylsulfonyl or alkoxysulfonyl radical, or $X_1$ and $X_2$ may be joined together, thus forming a saturated, partially unsaturated or totally unsaturated 4- to 8-membered ring optionally comprising one or more hetero atoms selected from the group consisting of sulfur, oxygen, nitrogen and phosphorus, $R_2$ and $R_3$ are independently selected from the group consisting of an alkyl radical comprising from 1 to 12 carbon atoms, a haloalkyl, cycloalkyl, halocycloalkyl, alkoxy, haloalkoxy, alkylthio, haloalkylthio, alkoxyalkyl, haloalkoxyalkyl, alkylthioalkyl, haloalkylthioalkyl, cyanoalkyl or acyl radical, a nitro, cyano, carboxyl, carbamoyl or 3-oxetanyloxycarbonyl radical, and an N-alkylcarbamoyl, N,N-dialkylcarbamoyl, alkoxycarbonyl, alkylthiocarbonyl, haloalkoxycarbonyl, alkoxythiocarbonyl, haloalkoxythiocarbonyl, alkylthiothiocarbonyl, alkenyl, alkynyl, N-alkylamino, N,N-dialkylamino, N-alkylaminoalkyl or N,N-dialkylaminoalkyl radical, or a radical chosen from aryl, arylalkyl, heterocyclyl and heterocyclylalkyl, optionally substituted with one or more radicals $R_9$ and/or aryl and/or arylalkyl, which may be identical or different, and/or a group $-T-R_8$, $R_1$, $R_4$, $R_5$, $R_6$ and $R_7$ are independently selected from the group consisting of a hydrogen atom, an optionally substituted alkyl radical comprising from 1 to 12 carbon atoms in a linear or branched chain, a haloalkyl, cycloalkyl, halocycloalkyl, alkoxy, aryloxy, arylalkoxy, haloalkoxy, alkylthio, haloalkylthio, alkoxyalkyl, haloalkoxyalkyl, alkylthioalkyl, haloalkylthioalkyl, cyanoalkyl or acyl radical, a nitro, cyano, carboxyl, carbamoyl or 3-oxetanyloxycarbonyl radical, and an N-alkylcarbamoyl, N,N-dialkylcarbamoyl, alkoxycarbonyl, alkylthiocarbonyl, haloalkoxycarbonyl, alkoxythiocarbonyl, haloalkoxythiocarbonyl, alkylthiothiocarbonyl, alkenyl, alkynyl, N-alkylamino, N,N-dialkylamino, N-alkylaminoalkyl or N,N-dialkylaminoalkyl radical, or a radical chosen from aryl, arylalkyl, heterocyclyl and heterocyclylalkyl, optionally substituted with one or more radicals $R_9$ and/or aryl and/or arylalkyl, which may be identical or different, and/or a group $-T-R_8$, or $R_4$ and $R_5$, on the one hand, or $R_6$ and $R_7$, on the other hand, may be joined together, thus forming a saturated, partially unsaturated or totally unsaturated 4- to 8-membered ring optionally comprising one or more hetero atoms chosen from sulfur, oxygen, nitrogen and phosphorus, T represents a direct bond or a divalent radical chosen from a radical —(CH$_2$)$_m$—, m taking a value between 1 and 12, limits included, the radical optionally being interrupted or ending with one or two hetero atoms selected from the group consisting of nitrogen, oxygen and/or sulfur, and an oxyalkylene, alkoxyalkylene, carbonyl (—CO—), oxycarbonyl (—O—CO—), carbonyloxy (—CO—O—), sulfinyl (—SO—), sulfonyl (—SO$_2$—), oxysulfonyl (—O—SO$_2$—), sulfonyloxy (—SO$_2$—O—), oxysulfinyl (—O—SO—), sulfinyloxy (—SO—O—), thio (—S—), oxy (—O—), vinyl (—C=C—), ethynyl (—C≡C—), —NR$_9$—, —NR$_9$O—, —ONR$_9$—, —N=N—, —NR$_9$—NR$_{10}$—, —NR$_9$—S—, —NR$_9$—SO—, —NR$_9$—SO$_2$—, —S—NR$_9$—, —SO$_2$—NR$_9$—, —SO$_2$—NR$_9$—, —CO—NR$_9$—O— and an —O—NR$_9$—CO— radical, $R_8$ is selected from the group consisting of a hydrogen atom and an aryl or heterocyclyl radical, $R_9$ and $R_{10}$, are independently selected from the group consisting of a hydrogen atom, a halogen atom, a hydroxyl, mercapto, nitro, thiocyanato, azido, cyano or pentafluorosulfonyl radical, and an alkyl, haloalkyl, alkoxy, haloalkoxy, alkylthio, haloalkylthio, alkoxyalkyl, haloalkoxyalkyl, alkylthioalkyl, haloalkylthioalkyl, arylalkyl, cyanoalkyl, cyanoalkoxy, cyanoalkylthio, alkylsulfinyl, haloalkylsulfinyl, alkylsulfonyl, haloalkylsulfonyl and an alkoxysulfonyl radical, as well as the optional N-oxides, geometrical and/or optical isomers, enantiomers and/or diastereoisomers, tautomeric forms, their salts or metal or metalloid complexes, wherein said process comprises reacting a compound of formula (II)

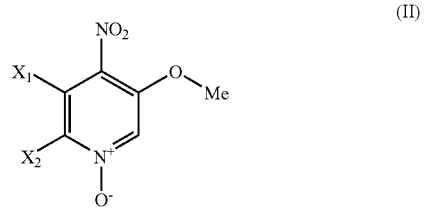

with a cyanide, alkali metal derivatives or alkaline-earth metal derivatives of hydrocyanic acid in the presence of an alkylating agent and a solvent, or with trimethylsilyl cyanide in the presence of dimethylcarbamoyl chloride and a solvent, to give a compound of formula (III)

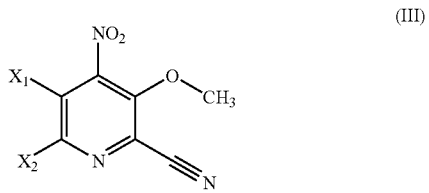

the compound of formula (III) above can be converted into a corresponding halo derivative of formula (IVa):

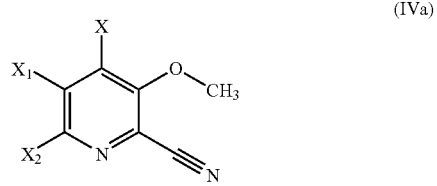

wherein X represents a halogen atom selected from the group consisting of fluorine, chlorine, bromine and iodine, by reaction with an acyl halide in the presence of a solvent, the halo derivative of formula (IVa) then being hydrolyzed to a compound of formula (Ia):

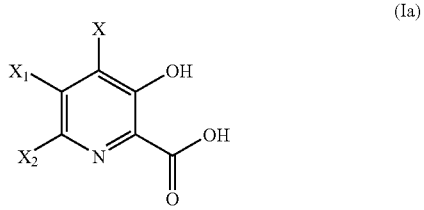

by the action of hot hydracid—or of a strong mineral base, optionally in the presence of aqueous hydrogen peroxide solution—and optionally of boron tribromide, the compounds of formula (III) or (IVa) can then optionally be placed in contact with an alcohol or an alkoxide in the presence of a solvent to give a compound of formula (IVb):

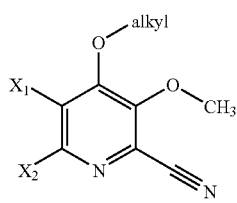

(IVb)

that is then hydrolyzed under operating conditions similar to those used for the formation of the compounds of formula (Ia), to give the compounds of respective formulae (Ib) and (Ib')

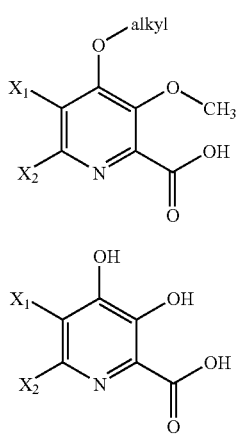

(Ib)

(Ib')

the compound of formula (IVa) can alternatively be converted into a picolinic acid derivative of formula (Va):

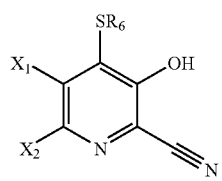

(Va)

by reacting a compound of formula $R_6SH$, or a corresponding alkali metal salt or alkaline-earth metal salt, in an aprotic polar solvent, at a temperature of between 0° C. and the boiling point of the solvent, the nitrile of formula (Va) then being hydrolyzed to give the corresponding acid of formula (Ic):

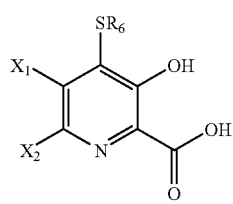

(Ic)

according to a reaction similar to that used to form the compound of formula (Ia), the halides of formula (IVa) can also optionally be treated with an azothydric acid salt at a temperature of between 0° C. and the boiling point of the solvent, to give the compound of formula (Vb):

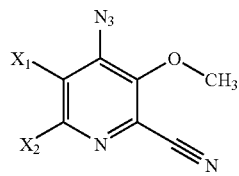

(Vb)

the compound of formula (Vb) can then optionally be hydrolyzed according to techniques similar to those presented for the preparation of the acids of formula (Ia) above, to give the acid of formula (Id):

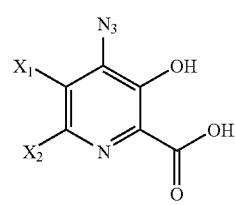

(Id)

the azides of formula (Id) then being optionally reduced to an amine derivative of formula (Ie):

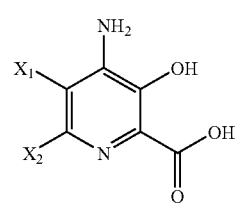

(Ie)

by the action of a reducing agent, the acids of formulae (Ia) to (Ie) can optionally be converted into thio acids, imino derivatives (—C(=NR$_1$)) or amino imino derivatives (—C(=N—NR$_4$R$_5$)) according to conventional techniques, the acids (Ia) to (Ie), or the thio, imino and imino-amino derivatives thereof defined above, substituted in position 3 (relative to the pyridine nitrogen atom) with —OH or -methoxy can optionally be subjected to various reactions known in the art to give the corresponding derivatives substituted in position 3 (relative to the pyridine nitrogen atom) with —O—Z, the compound of formula (I) wherein Y represents an amino radical (—NH$_2$) can optionally be placed in contact with an acylating agent in the presence of a solvent and optionally of a base, to give the compounds of formulae (VIa) and (VIb):

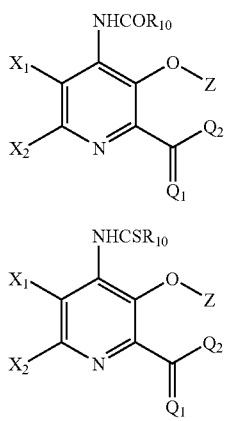

(VIa)

(VIb)

the picolinic acid derivative of formula (VII):

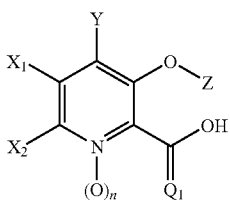

(VII)

can optionally be placed in contact with a reagent of formula R$_2$OH, R$_3$SH or HNR$_4$R$_5$, at a temperature between −80° C. and 180° C. or at the boiling point of the solvent, to give the respective compounds of formulae (VIIIa), (VIIIb) and (VIIIc), which form the set of compounds of formula (VIII):

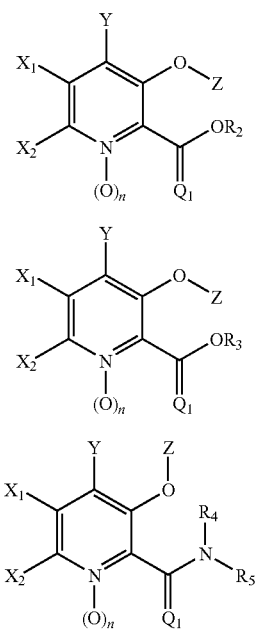

(VIIIa)

(VIIIb)

(VIIIc)

which are special cases of the compound of formula (I) in which Q$_2$ represents —OR$_2$, —SR$_3$ and —NR$_4$R$_5$, respectively, the compounds of general formula (IX):

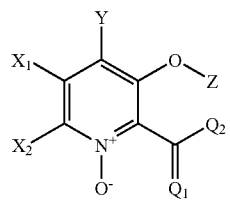

(IX)

which are special cases of the compound of formula (I) for which n is equal to 1, can optionally be obtained by a process comprising placing a compound of formula (X):

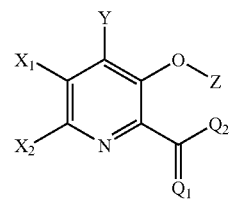

(X)

which is a special case of the compounds of formula (I) for which n is equal to zero, in contact with an oxidizing agent, aqueous hydrogen peroxide solution or carboxylic, boronic or sulfuric peracids.

2. The process of claim 1 wherein the solvent used for the halogenation reaction of the compound of formula (III) to the compound of formula (IV) is selected from the group consisting of diethyl ether, diisopropyl ether, tetrahydrofuran, dioxane and 1,2-dimethoxyethane.

3. The process of claim 1 wherein the hydrolysis reaction of the compound of formula (IV) into the compound of formula (Ia) comprises treating the nitrile of formula (IVa) with an excess of acid in the absence or presence of a solvent, at reflux or at a temperature of between 20° C. and 200° C.

4. The process of claim 3 wherein the acid is selected from the group consisting of hydrochloric acid, hydriodic acid, hydrobromic acid and alkylsulfonic acids.

5. The process of claim 1 wherein the solvent used in the reaction for conversion of the compound of formula (IVa) into the compound of formula (Va) is selected from the group consisting of dimethylformamide, dimethylacetamide, N-methylpyrrolidone, dimethvlpropyleneurea and dimethyl sulfoxide.

6. The process of claim 1 wherein the solvent used in the reaction for conversion of the compound of formula (IVa) into the compound of formula (Vb) is selected from the group consisting of dimethylformamide, dimethylacetamide, N-methylpyrrolidone, dimethvlpropyleneurea and dimethyl sulfoxide.

7. The process of claim 1 wherein the reducing agent used for the reduction of the compound of formula (Id) to the compound of formula (Ie) is selected from the group consisting of lithium aluminum hydride, triphenylphosphine and hydrogen in the presence of a catalyst.

8. The process of claim 1 wherein the acylating agent used in the step for preparing the compounds of formulae (VIa) and (VIb) is selected from the group consisting of an acyl halide, an anhydride, an acid, an ester and a primary amide, and thio homologues thereof.

9. The process of claim 1 wherein the activating agent used for the formation of the compound of formula (VIII) is selected from the group consisting of thionyl chloride, oxalyl chloride, dicyclocarbodiimide, 1-(3-dimethylamino-propyl)-3-ethylcarbodiimide hydrochloride, 1-hydroxybenzotriazole and phosphorus oxychloride.

10. The process of claim 1 wherein the solvent used in the reaction for obtaining the compounds of formula (VIII) is selected from the group consisting of pentane, hexane, heptane, octane, benzene, toluene, xylenes, halobenzenes, diethyl ether, diisopropyl ether, tetrahydrofuran, dioxane, dimethoxyethane, dichloromethane, chloroform, 1,2-dichloroethane, 1,1,1-trichloroethane, methyl acetate, ethyl acetate, acetonitrile, propionitrile, benzonitrile, dimethylformamide, dimethylacetamide, N-methylpyrrolidone, dimethylpropyleneurea, dimethyl sulfoxide, pyridine and water and mixtures of the foregoing.

11. The process of claim 1 wherein the reaction time for obtaining the compounds of formula (VIII) is between 0.1 and 48 hours.

12. The process of claim 1 wherein the reaction for obtaining the compounds of formula (VIII) is performed in the presence of an organic or mineral base selected from the group consisting of alkali metal hydroxides and alkaline-earth metal hydroxides, alkali metal alkoxides and alkaline-earth metal alkoxides, alkali metal hydrides and alkaline-earth metal hydrides, alkali metal carbonates and bicarbonates and alkaline-earth metal carbonates and bicarbonates, and organonitrogen bases.

13. The process in of claim 12 wherein the organic or mineral base is selected from the group consisting of sodium hydroxide, potassium hydroxide, cesium hydroxide, calcium hydroxide, potassium tert-butoxide, sodium hydride, potassium hydride, caesium hydride, sodium carbonate, potassium carbonate, calcium carbonate, sodium bicarbonate, potassium bicarbonate, calcium bicarbonate, pyridine, trimethylamine, triethylamine, or diisopropylethylamine, 1,5-diazobicyclo[4.3.0]non-5-ene and 1,8-diazabicyclo-[5.4.0]undec-7-ene.

14. The process of claim 11 wherein an excess of liquid base selected from the group consisting of pyridine and alkylpyridines is used, thus replacing the solvent.

15. The process of claim 1 wherein $X_1$ and $X_2$ each represents a hydrogen atom.

16. The process of claim 1 wherein $Q_1$ is selected from the group consisting of an oxygen atom and a sulfur atom.

17. The process of claim 1 wherein Z is selected from the group consisting of an alkyl radical, a hydrogen atom and an alkoxyalkyl, haloalkoxyalkyl, alkylthioalkyl, haloalkylthioalkyl, N-alkylaminoalkyl, N,N-dialkylaminoalkyl, acylaminoalkyl, acyl, thioacyl, cyanoalkyl, alkoxythiocarbonyl, N-alkylaminothiocarbonyl, N,N-dialkylaminothiocarbonyl and an alkylsulfinyl radical.

18. The process of claim 1 wherein Y is selected from the group consisting of a hydrogen atom, a halogen atom, a hydroxyl, mercapto, nitro, thiocyanato, azido, cyano or pentafluorosulfonyl radical, an alkyl, haloalkyl, alkoxy, haloalkoxy, alkylthio, haloalkylthio, alkoxyalkyl, haloalkoxyalkyl, alkylthioalkyl, haloalkylthioalkyl, alkylsulfinyl, haloalkylsulfinyl, alkylsulfonyl, haloalkylsulfonyl or alkoxysulfonyl radical, and an amino, N-alkylamino, N,N-dialkylamino, —$NHCOR_{10}$, —$NHCSR_{10}$, N-arylamino, N,N-diarylamino, arylcarbonylamino, arylthiocarbonylamino, aryloxythiocarbonylamino and an N,N-arylalkylaminothiocarbonylamino group.

19. The process of claim 1 wherein $Q_2$ represents a group —$NR_4R_5$, in which $R_4$ represents a hydrogen atom and $R_5$ is selected from the group consisting of an optionally substituted alkyl radical containing from 1 to 12 carbon atoms in a linear or branched chain, haloalkyl, alkoxy, haloalkoxy, alkylthio, haloalkylthio, alkenyl and alkynyl and a radical selected from the group consisting of aryl, arylalkyl, heterocyclyl and heterocyclylalkyl, optionally substituted with one or more radicals $R_9$ and/or -aryl and/or arylalkyl, which may be identical or different, and/or a group -T-$R_8$.

20. The process of claim 1 wherein:

$X_1$ and $X_2$ each represent represents a hydrogen atom,

Z is selected from the group consisting of an alkyl radical, a hydrogen atom and an alkoxyalkyl, haloalkoxyalkyl, alkylthioalkyl, haloalkylthioalkyl, N-alkylaminoalkyl, N,N-dialkylaminoalkyl, acylaminoakyl, acyl, thioacyl, cyanoalkyl, alkoxythiocarbonyl, N-alkylaminothiocarbonyl, N,N-dialkylaminothiocarbonyl and an alkylsulfinyl radical, Y is selected from the group consisting of a hydrogen atom, a halogen atom, a hydroxyl, mercapto, nitro, thiocyanato, azido, cyano, or pentafluorosulfonyl radical, an alkyl, haloalkyl, alkoxy, haloalkoxy, alkylthio, haloalkylthio, alkoxyalkyl, haloalkoxyalkyl, alkylthioalkyl, haloalkylthioalkyl, alkylsulfinyl, haloalkylsulfinyl, alkylsulfonyl, haloalkylsulfonyl or alkoxysulfonyl radical, and an amino, N-alkylamino, N,N-dialkylamino, —$NHCOR_{10}$, —$NHCSR_{10}$, N-arylamino, N,N-diarylamino, arylcarbonylamino, aryithiocarbonylamino, aryloxythiocarbonylamino or N,N-arylalkylaminothiocarbonylamino group, $Q_1$ is selected from the group consisting of an oxygen atom and a sulfur atom, $Q_2$ represents a group —$NR_4R_5$, in which $R_4$ represents a hydrogen atom and $R_5$ is selected from the group consisting of an optionally substituted alkyl radical containing from 1 to 12 carbon atoms in a linear or branched chain, haloalkyl, alkoxy, haloalkoxy, alkylthio, haloalkylthio, alkenyl and alkynyl and a radical chosen from aryl, arylalkyl, heterocyclyl and heterocyclylalkyl, optionally substituted with one or more radicals $R_9$ and/or aryl and/or arylalkyl, which may be identical or different, and/or a group -T-$R_8$.

21. The process of claim 3 wherein:

$X_1$ and $X_2$ each represent represents a hydrogen atom,

Z is selected from the group consisting of an alkyl radical, a hydrogen atom and an alkoxyalkyl, haloalkoxyalkyl, alkylthioalkyl, haloalkylthioalkyl, N-alkylaminoalkyl, N,N-dialkylaminoalkyl, acylaminoalkyl, acyl, thioacyl, cyanoalkyl, alkoxythiocarbonyl, N-alkylaminothiocarbonyl, N,N-dialkylaminothiocarbonyl and an alkylsulfinyl radical, Y is selected from the group consisting of a hydrogen atom, a halogen atom, a hydroxyl, mercapto, nitro, thiocyanato, azido, cyano or pentafluorosulfonyl radical, an alkyl, haloalkyl, alkoxy, haloalkoxy, alkylthio, haloalkylthio, alkoxyalkyl, haloalkoxyalkyl, alkylthioalkyl, haloalkylthioalkyl, alkylsulfinyl, haloalkylsulfinyl, alkylsulfonyl, haloalkylsulfonyl or alkoxysulfonyl radical, and an amino, N-alkylamino, N,N-dialkylamino, —$NHCOR_{10}$, —$NHCSR_{10}$, N-arylamino, N,N-diarylamino, arylcarbonylamino, arylthiocarbonylamino, aryloxythiocarbonylamino and an N,N-arylalkylaminothiocarbonylamino group, $Q_1$ is selected from the group consistina of an oxygen atom and a sulfur atom, $Q_2$ represents a group —$NR_4R_5$, in which $R_4$ represents a hydrogen atom and $R_5$ is selected from the group consisting of an optionally substituted alkyl radical containing from 1 to 12 carbon atoms in a linear or branched chain, haloalkyl, alkoxy, haloalkoxy, alkylthio, haloalkylthio, alkenyl and alkynyl and a radical selected from the group consisting of aryl, arylalkyl, heterocyclyl and heterocyclylalkyl, optionally substituted with one or more radicals $R_9$ and/or aryl and/or arylalkyl, which may be identical or different, and/or a group -T-$R_8$.

22. The process of claim 1 wherein:

$X_1$ and $X_2$ each represents a hydrogen atom,

Z is selected from the group consisting of an alkyl radical, a hydrogen atom and an alkoxyalkyl, haloalkoxyalkyl, alkylthioalkyl, haloalkylthioalkyl, N-alkylaminoalkyl, N,N-dialkylaminoalkyl, acylaminoalkyl, acyl, thioacyl, cyanoalkyl, alkoxythiocarbonyl, N-alkylaminothiocarbonyl, N,N-dialkylaminothiocarbonyl and an alkylsulfinyl radical, Y is selected from the group consisting of a hydrogen atom, a halogen atom, a hydroxyl, azido, alkoxy, alkylthio or alkylsulfonyl radical and an amino, —$NHCOR_{10}$ and —$NHCSR_{10}$ group, $Q_1$ represents an oxygen atom, $Q_2$ represents a group $NR_4R_5$, in which $R_4$ represents a hydrogen atom and $R_5$ is selected from the group consisting of an aryl, arylalkyl, heterocyclyl and heterocyclylalkyl radical, optionally substituted with one or more radicals $R_9$ and/or aryl and/or arylalkyl, which may be identical or different, and/or a group -T-$R_8$.

23. The process of claim 1 wherein the 3-hydroxypicolinic acid derivative compound of formula (I) is selected from the group consisting of:

3-hydroxy-N-{[3-(trifluoromethyl)benzyl]oxy}-2-pyridine carboxamide,

1-{3-hydroxy-2-[(4-phenoxyanilino)carbonyl]-4-pyridinyl}-1,2-triazadien-2-ium, 4-amino-3-hydroxy-N-{4-[4-(trifluoromethyl)-phenoxy]phenyl}-2-pyridine carboxamide, 4-amino-3-hydroxy-N-[4-(4-methylphenoxy)phenyl]-2-pyridine carboxamide, 4-(formylamino)-3-hydroxy-N-{4-[3-(trifluoromethyl)phenoxy]phenyl}-2-pyridine carboxamide, N-[4-(4-chlorophenoxy)phenyl]-4-(formylamino)-3-hydroxy-2-pyridine carboxamide, 4-(formylamino)-3-hydroxy-N-{4-[4-(trifluoromethyl)phenoxy]phenyl}-2-pyridine carboxamide and N-[4-(benzyloxy)phenyl]-4-(formylamino)-3-hydroxy-2-pyridine carboxamide, and the possible N-oxides, geometrical and/or optical isomers, enantiomers and/or diastereoisomers, tautomeric forms salts or metallic or metalloid complexes thereof.

* * * * *